(12) United States Patent
Mishelevich et al.

(10) Patent No.: US 8,956,273 B2
(45) Date of Patent: Feb. 17, 2015

(54) FIRING PATTERNS FOR DEEP BRAIN TRANSCRANIAL MAGNETIC STIMULATION

(75) Inventors: David J. Mishelevich, San Mateo, CA (US); M. Bret Schneider, San Mateo, CA (US)

(73) Assignee: Cervel Neurotech, Inc., Redwood City, CA (US)

( * ) Notice: Subject to any disclaimer, the term of this patent is extended or adjusted under 35 U.S.C. 154(b) by 1140 days.

(21) Appl. No.: 12/670,938

(22) PCT Filed: Aug. 20, 2008

(86) PCT No.: PCT/US2008/073751
§ 371 (c)(1),
(2), (4) Date: Jun. 17, 2010

(87) PCT Pub. No.: WO2009/026386
PCT Pub. Date: Feb. 26, 2009

(65) Prior Publication Data

US 2010/0256438 A1   Oct. 7, 2010

Related U.S. Application Data

(60) Provisional application No. 60/956,920, filed on Aug. 20, 2007, provisional application No. 60/970,958, filed on Sep. 9, 2007, provisional application No. 61/077,488, filed on Jul. 2, 2008.

(51) Int. Cl.
*A61N 1/00* (2006.01)
*A61B 17/52* (2006.01)
*A61N 2/00* (2006.01)

(52) U.S. Cl.
CPC ...................................... *A61N 2/006* (2013.01)
USPC .................. 600/13; 600/9; 128/897; 128/898; 128/899

(58) Field of Classification Search
CPC ......... A61N 2/02; A61N 2/006; A61N 2/004; A61N 2/00; A61N 1/0456
USPC ........................................ 600/13, 9; 128/898
See application file for complete search history.

(56) References Cited

U.S. PATENT DOCUMENTS 3,799,164 A   3/1974   Rollins
4,134,395 A   1/1979   Davis
(Continued)

FOREIGN PATENT DOCUMENTS

DE   10242542 A1   4/2004
EP   0501048 A1   9/1992
(Continued)

OTHER PUBLICATIONS

Aleman et al.; Efficacy of slow repetitive transcranial magnetic stimulation in the treatment of resistant auditory hallucinations in schizophrenia: a meta-analysis; J Clin Psychiatry; 68(3):416-21; Mar. 2007.

(Continued)

*Primary Examiner* — Christine Matthews
*Assistant Examiner* — Sunita Reddy
(74) *Attorney, Agent, or Firm* — Shay Glenn LLP

(57) ABSTRACT

Methods, devices and systems for Transcranial Magnetic Stimulation (TMS) are provided for synchronous, asynchronous, or independent triggering the firing multiple of electromagnets from either a single power source or multiple energy sources. These methods are particularly useful for stimulation of deep (e.g., sub-cortical) brain regions, or for stimulation of multiple brain regions, since controlled magnetic pulses reaching the deep target location may combine to form a patterned pulse train that activates the desired volume of target tissue. Furthermore, the methods, devices and systems described herein may be used to control the rate of firing of action potentials in one or more brain regions, such as slow or fast rate rTMS. For example, described herein are multiple electromagnetic stimulation sources, each of which are activated independently to create a cumulative effect at the intersections of the electromagnetic stimulation trajectories, typically by means of a computerized calculation.

14 Claims, 11 Drawing Sheets

(56) References Cited

U.S. PATENT DOCUMENTS

| | | | |
|---|---|---|---|
| 4,889,526 A | 12/1989 | Rauscher et al. | |
| 5,207,223 A | 5/1993 | Adler | |
| 5,267,938 A | 12/1993 | Konotchick | |
| 5,427,097 A | 6/1995 | Depp | |
| 5,441,495 A | 8/1995 | Liboff et al. | |
| 5,531,227 A | 7/1996 | Schneider | |
| 5,707,334 A | 1/1998 | Young | |
| 5,738,625 A | 4/1998 | Gluck | |
| 5,766,124 A | 6/1998 | Polson | |
| 5,891,034 A | 4/1999 | Bucholz | |
| 6,042,531 A | 3/2000 | Holcomb | |
| 6,132,361 A | 10/2000 | Epstein et al. | |
| 6,132,631 A | 10/2000 | Nallan et al. | |
| 6,149,577 A | 11/2000 | Bouldin et al. | |
| 6,179,770 B1 | 1/2001 | Mould | |
| 6,179,771 B1 | 1/2001 | Mueller | |
| 6,198,958 B1 | 3/2001 | Ives et al. | |
| 6,236,875 B1 | 5/2001 | Bucholz et al. | |
| 6,266,556 B1 | 7/2001 | Ives et al. | |
| 6,351,573 B1 | 2/2002 | Schneider | |
| 6,356,781 B1 | 3/2002 | Lee et al. | |
| 6,425,852 B1 | 7/2002 | Epstein et al. | |
| 6,447,440 B1 | 9/2002 | Markoll | |
| 6,461,289 B1 | 10/2002 | Muntermann | |
| 6,488,617 B1 * | 12/2002 | Katz | 600/26 |
| 6,507,751 B2 | 1/2003 | Blume et al. | |
| 6,537,197 B1 | 3/2003 | Ruohonen et al. | |
| 6,571,123 B2 | 5/2003 | Ives et al. | |
| 6,572,528 B2 | 6/2003 | Rohan et al. | |
| 6,663,556 B2 | 12/2003 | Barker | |
| 6,818,669 B2 | 11/2004 | Moskowitz et al. | |
| 6,849,040 B2 | 2/2005 | Ruohonen et al. | |
| 6,858,000 B1 | 2/2005 | Naraikin et al. | |
| 6,972,097 B2 | 12/2005 | Yoshida et al. | |
| 7,023,311 B2 | 4/2006 | Baldwin et al. | |
| 7,087,008 B2 | 8/2006 | Fox et al. | |
| 7,088,210 B2 | 8/2006 | Day et al. | |
| 7,104,947 B2 | 9/2006 | Riehl | |
| 7,141,028 B2 | 11/2006 | McNew | |
| 7,153,256 B2 | 12/2006 | Riehl et al. | |
| 7,155,284 B1 | 12/2006 | Whitehurst et al. | |
| 7,236,830 B2 | 6/2007 | Gliner | |
| 7,239,910 B2 | 7/2007 | Tanner | |
| 7,367,935 B2 | 5/2008 | Mechlenburg et al. | |
| 7,367,936 B2 | 5/2008 | Myers et al. | |
| 7,396,326 B2 | 7/2008 | Riehl et al. | |
| 7,437,196 B2 | 10/2008 | Wyler et al. | |
| 7,483,747 B2 | 1/2009 | Gliner et al. | |
| 7,520,848 B2 | 4/2009 | Schneider et al. | |
| 7,771,341 B2 | 8/2010 | Rogers | |
| 7,856,264 B2 | 12/2010 | Firlik et al. | |
| 7,904,134 B2 | 3/2011 | McIntyre et al. | |
| 2002/0022777 A1 | 2/2002 | Crieghton et al. | |
| 2002/0042563 A1 | 4/2002 | Becerra et al. | |
| 2002/0097125 A1 | 7/2002 | Davey | |
| 2003/0004392 A1 | 1/2003 | Tanner et al. | |
| 2003/0028072 A1 | 2/2003 | Fischell et al. | |
| 2003/0065243 A1 | 4/2003 | Tanner | |
| 2003/0204135 A1 | 10/2003 | Bystritsky | |
| 2004/0010177 A1 | 1/2004 | Rohan et al. | |
| 2004/0077921 A1 | 4/2004 | Becker et al. | |
| 2004/0078056 A1 | 4/2004 | Zangen et al. | |
| 2004/0193000 A1 | 9/2004 | Riehl | |
| 2004/0193002 A1 | 9/2004 | Tanner et al. | |
| 2005/0033154 A1 | 2/2005 | deCharms | |
| 2005/0038313 A1 | 2/2005 | Ardizzone | |
| 2005/0046532 A1 | 3/2005 | Dodd | |
| 2005/0107655 A1 | 5/2005 | Holzner | |
| 2005/0113630 A1 | 5/2005 | Fox et al. | |
| 2005/0124848 A1 | 6/2005 | Holzner | |
| 2005/0148808 A1 | 7/2005 | Cameron et al. | |
| 2005/0154426 A1 | 7/2005 | Boveja et al. | |
| 2005/0222625 A1 | 10/2005 | Laniado et al. | |
| 2005/0234286 A1 | 10/2005 | Riehl et al. | |
| 2005/0256539 A1 | 11/2005 | George et al. | |
| 2006/0058853 A1 | 3/2006 | Bentwich | |
| 2006/0094924 A1 | 5/2006 | Riehl et al. | |
| 2006/0106430 A1 * | 5/2006 | Fowler et al. | 607/45 |
| 2006/0122454 A1 | 6/2006 | Riehl et al. | |
| 2006/0122496 A1 | 6/2006 | George et al. | |
| 2006/0149337 A1 | 7/2006 | John | |
| 2006/0173274 A1 | 8/2006 | George et al. | |
| 2006/0189866 A1 | 8/2006 | Thomas et al. | |
| 2006/0199992 A1 | 9/2006 | Eisenberg et al. | |
| 2006/0218790 A1 | 10/2006 | Day et al. | |
| 2006/0287566 A1 * | 12/2006 | Zangen et al. | 600/15 |
| 2007/0027353 A1 | 2/2007 | Ghiron et al. | |
| 2007/0027504 A1 | 2/2007 | Barrett et al. | |
| 2007/0083074 A1 | 4/2007 | Sotiriou | |
| 2007/0100392 A1 | 5/2007 | Maschino et al. | |
| 2007/0100398 A1 | 5/2007 | Sloan | |
| 2007/0242406 A1 | 10/2007 | Annis et al. | |
| 2007/0260107 A1 | 11/2007 | Mishelevich | |
| 2007/0265489 A1 | 11/2007 | Fowler et al. | |
| 2007/0293916 A1 | 12/2007 | Peterchev | |
| 2008/0033297 A1 | 2/2008 | Sliwa | |
| 2008/0058582 A1 | 3/2008 | Aho et al. | |
| 2008/0064950 A1 | 3/2008 | Ruohonen et al. | |
| 2008/0123922 A1 * | 5/2008 | Gielen et al. | 382/131 |
| 2008/0161636 A1 | 7/2008 | Hurme et al. | |
| 2008/0306325 A1 | 12/2008 | Epstein | |
| 2009/0018384 A1 | 1/2009 | Boyden et al. | |
| 2009/0024021 A1 | 1/2009 | George et al. | |
| 2009/0099405 A1 | 4/2009 | Schneider et al. | |
| 2009/0099623 A1 | 4/2009 | Bentwich | |
| 2009/0112133 A1 | 4/2009 | Deisseroth et al. | |
| 2009/0112277 A1 | 4/2009 | Wingeier et al. | |
| 2009/0114849 A1 | 5/2009 | Schneider et al. | |
| 2009/0124848 A1 | 5/2009 | Miazga | |
| 2009/0156884 A1 | 6/2009 | Schneider et al. | |
| 2009/0187062 A1 | 7/2009 | Saitoh | |
| 2009/0189470 A1 | 7/2009 | McClellan | |
| 2009/0227830 A1 | 9/2009 | Pillutla et al. | |
| 2009/0234243 A1 | 9/2009 | Schneider et al. | |
| 2010/0004500 A1 | 1/2010 | Gliner et al. | |
| 2010/0210894 A1 | 8/2010 | Pascual-Leone et al. | |
| 2011/0082326 A1 | 4/2011 | Mishelevich et al. | |
| 2011/0184223 A1 | 7/2011 | Peterchev et al. | |
| 2011/0273251 A1 | 11/2011 | Mishelevich et al. | |
| 2012/0016177 A1 | 1/2012 | Mishelevich et al. | |
| 2013/0096363 A1 | 4/2013 | Schneider et al. | |
| 2013/0267763 A1 | 10/2013 | Schneider et al. | |
| 2013/0317281 A1 | 11/2013 | Schneider et al. | |
| 2014/0200388 A1 | 7/2014 | Schneider et al. | |

FOREIGN PATENT DOCUMENTS

| | | |
|---|---|---|
| EP | 0709115 A1 | 5/1996 |
| EP | 0788813 A1 | 8/1997 |
| EP | 1326681 B1 | 1/2007 |
| GB | 2271931 A | 5/1994 |
| GB | 2336544 A | 10/1999 |
| JP | 64-046479 | 2/1989 |
| JP | 5-237197 | 9/1993 |
| JP | 2003-180649 | 7/2003 |
| JP | 2003-205040 | 7/2003 |
| KR | 10-0457104 | 11/2004 |
| WO | WO 98/56302 A1 | 12/1998 |
| WO | WO 99/39769 A1 | 8/1999 |
| WO | WO 99/55421 A2 | 11/1999 |
| WO | WO 00/74777 A1 | 12/2000 |
| WO | WO 00/78267 A2 | 12/2000 |
| WO | WO 02/09811 A1 | 2/2002 |
| WO | WO 02/32504 A2 | 4/2002 |
| WO | WO 03/082405 A1 | 10/2003 |
| WO | WO 2004/087255 A1 | 10/2004 |
| WO | WO 2005/000153 A2 | 1/2005 |
| WO | WO 2006/124914 A2 | 11/2006 |
| WO | WO 2007/050592 A2 | 5/2007 |
| WO | WO 2007/130308 A2 | 11/2007 |

(56) References Cited

FOREIGN PATENT DOCUMENTS

WO     WO 2009/042863 A1     4/2009

OTHER PUBLICATIONS

Alonso et al.; Right prefrontal repetitive transcranial magnetic stimulation in obsessive-compulsive disorder: a double-blind, placebo-controlled study; Am J Psychiatry; 158(7):1143-5; Jul. 2001.
Antal et al.; Transcranial Direct Current Stimulation Over Somatosensory Cortex Decreases Experimentally Induced Acute Pain Perception; Clin J Pain; vol. 24, No. 1; pp. 56-63; Jan. 2008.
Boggioa et al.; A randomized, double-blind clinical trial on the efficacy of cortical direct current stimulation for the treatment of major depression; International Journal of Neuropsychopharmacology; 11(2): 249-254; Mar. 2008.
Cohen et al.; Repetitive transcranial magnetic stimulation of the right dorsolateral prefrontal cortex in posttraumatic stress disorder: a double-blind, placebo-controlled study; Am J Psychiatry; 161(3):515-24; Mar 2004.
Fecteau et al.; Diminishing risk-taking behavior by modulating activity in the prefrontal cortex: a direct current stimulation study; J Neurosci.; 27(46):12500-5; Nov. 14, 2007.
Fitzgerald et al.; Transcranial magnetic stimulation in the treatment of depression: a double-blind, placebo-controlled trial; Arch Gen Psychiatry; 60(10):1002-8; Oct. 2003.
Fregni et al.; Anodal transcranial direct current stimulation of prefrontal cortex enhances working memory; Exp Brain Res.; 166(1); pp. 23-30; Sep 2005.
Khedr et al.; Therapeutic effect of repetitive transcranial magnetic stimulation on motor function in Parkinson's disease patients; Eur J Neurol; 10(5):567-72; Sep. 2003.
Kleinjung et al.; Transcranial magnetic stimulation: a new diagnostic and therapeutic tool for tinnitus patients; Int Tinnitus J.; 14(2)1 12-8; Jul./Dec. 2008.
Lang et al.; Bidirectional Modulation of Primary Visual Cortex Excitability: A Combined tDCS and rTMS Study; Investigative Ophthalmology and Visual Science; 48(12): 5782-5787; Dec. 2007.
Lang et al.; Preconditioning with Transcranial Direct Current Stimulation Sensitizes the Motor Cortex to Rapid-Rate Transcranial Magnetic Stimulation and Controls the Direction of After-Effects; Biol. Psychiatry; 56(9): 634-639; Nov. 1, 2004.
Mansur et al.; A sham stimulation-controlled trial of rTMS of the unaffected hemisphere in stroke patients; Neurology; 64(10):1802-4; May 24, 2005.
Nitsche et al.; Excitability changes induced in the human motor cortex by weak transcranial direct current stimulation; Journal of Physiology; 527(3):633-639; Sep. 15, 2000.
O'Reardon et al.; Efficacy and safety of transcranial magnetic stimulation in the acute treatment of major depression: a multisite randomized controlled trial; Biol Psychiatry; 62(11):1208-16; Dec. 1, 2007.
Ragert et al.; Improvement of spatial tactile acuity by transcranial direct current stimulation; Clin. Neurophysiol.; 119(4):805-11; Apr. 2008 (author manuscript).
Roizenblatt et al.; Site-specific Effects of Transcranial Direct Current Stimulation on Sleep and Pain in Fibromyalgia: A Randomized, Sham-controlled study; Pain Practice; 7(4): 297-306; Dec. 7, 2007.
Sparing et al.; Enhancing language performance with non-invasive brain stimulation R A transcranial direct current stimulation study in healthy humans; Neuropsychologia; 46(1): 261-268; Jan. 15, 2008.
Theodore et al.; Transcranial magnetic stimulation for the treatment of seizures: a controlled study; Neurology; 59(4):560-2; Aug. 27, 2002.
Zanette et al.; The effect of repetitive transcranial magnetic stimulation on motor performance, fatigue and quality of life in amyotrophic lateral sclerosis; J Neurol Sci.; 270(1-2):18-22; Jul. 15, 2008.
Dantec magnetic stimulation product information on MagPro X100 with MagOption; http://www.danica.nl/neuro/neuro-magnetische-stimulatoren.htm; Jan. 15, 2009.
Hayward et al.; The role of the anterior cingulate cortex in the counting stroop task; Exp Brain Res; vol. 154(3); pp. 355-358; Feb. 2004.
Hsu et al., Analysis of Efficiency of Magnetic Stimulation; IEEE Transactions on Biomedical Engineering; vol. 50, No. 11; Sep. 2003; pp. 1276-1285.
Kamitani et al.; A model of magnetic stimulation of neocortical neurons; Neurocomputing; vol. 38; No. 40; Jun. 2001; pp. 697-703.
Kandel et al.; Chapter 12: Synaptic Integration; Principles of Neural Science; Editors: Kandel, Schwartz and Jessell; 4th Edition, McGraw-Hill; pp. 208-227; Jan. 5, 2000.
Lefaucheur, Jean-Pascal; Use of repetitive transcranial magnetic stimulation in pain relief; Expert Rev Neurother; vol. 8, No. 5: pp. 799-808; May 2008.
Lefaucheur et al.; Pain relief induced by repetitive transcranial magnetic stimulation of precentral cortex; Neuroreport; vol. 12, issue 13: pp. 2963-2965; Sep. 17, 2001.
Lefaucheur et al.; Somatotopic organization of the analgesic effects of motor cortex rTMS in neuropathic pain; Neurology; vol. 67, No. 11: pp. 1998-2004; Dec. 12, 2006.
Levkovitz et al.; A randomized controlled feasibility and safety study of deep transcranial magnetic stimulation; Clin. Neurophysiol.; vol. 118(12); pp. 2730-2744; Dec. 2007.
Miranda et al.; The Electric Field Induced in the Brain by Magnetic Stimulation: A 3-D Finite-Element Analysis of the Effects of Tissue Heterogeneity and Anisotropy; IEEE Transactions on Biomedical Engineering; vol. 50; No. 9; Sep. 2003; pp. 1074-1085.
Rossini et al.; Transcranial magnetic stimulation: Diagnostic, therapeutic, and research potential; Neurology; vol. 68, No. 7: pp. 484-488; Feb. 13, 2007.
Ruohonen, J.; Transcranial magnetic stimulation: modelling and new techniques; (doctoral dissertation); Helsinki Univ. of Tech.; Dept. of Eng. Physics and Mathematics; Espoo, Finland; Dec. 1998.
Wagner et al.; Transcranial direct current stimulation: A computer-based human model study; NeuroImage; vol. 35; issue 3; Apr. 15, 2007; pp. 1113-1124.
Yang et al.; 3D Realistic Head Model Simulation Based on Transcranial Magnetic Stimulation; Conf Proc IEEE Eng Med Biol Soc.; vol. Suppl.; Aug. 30-Sep. 3, 2006; 4 pages.
Yu et al.; Pathogenesis of normal-appearing white matter damage in neuromyelitis optica: diffusion-tensor MR imaging; Radiology; vol. 246, No. 1: pp. 222-228; Jan. 2008.
Mishelevich et al.; U.S. Appl. No. 12/990,235 entitled "Transcranial magnetic stimulation by enhanced magnetic field perturbations," filed Oct. 29, 2010.
Schneider, M. Bret.; U.S. Appl. No. 13/169,967 entitled "Enhanced Spatial Summation for Deep-Brain Transcranial Magnetic Stimulation," filed Jun. 27, 2011.
Sadler, John W.; U.S. Appl. No. 13/512,496 entitled "Power Management in Transcranial Magnetic Stimulators," filed Sep. 17, 2012.
Schneider et al.; U.S. Appl. No. 13/586,640 entitled "Transcranial Magnet Stimulation of Deep Brain Targets," filed Aug. 15, 2012.
Agnew et al.; Considerations for safety in the use of extracranial stimulation for motor evoked potentials; Neurosurgery; vol. 20; pp. 143-147; 1987.
Avery et al.; A Controlled Study of Repetitive Transcranial Magnetic Stimulation in Medication-Resistant Major Depression; Biological Psychiatry; vol. 59; pp. 187-194; 2005.
Barker et al.; Non invasive magnetic stimulation of the human motor cortex; Lancet; vol. 1; pp. 1106-1110; 1985.
Barker, A. T.; An introduction to the basic principles of magnetic nerve stimulation; Journal of Clinical Neurophysiology; vol. 8; No. 1; pp. 26-37; 1991.
Basser et al.; Stimulation of myelinated nerve axon by electromagnetic induction; Medical & Biological Engineering and Computing.; vol. 29; pp. 261-268; 1991.
Bohning et al.; Mapping transcranial magnetic stimulation (TMS) fields in vivo with MRI; NeuroReport; vol. 8; No. 11; pp. 2535-2538; Jul. 28, 1997.
Conca et al.; Effect of chronic repetitive transcranial magnetic stimulation on regional cerebral blood flow and regional cerebral glucose uptake in drug treatment-resistant depressives. A brief report; Neuropsychobiology; vol. 45; No. 1; pp. 27-31; 2002.
Davey et al.; Designing transcranial magnetic stimulation systems; IEEE Transactions on Magnetics; vol. 41; No. 3; pp. 1142-1148; Mar. 2005.

(56) References Cited

OTHER PUBLICATIONS

Davey et al.; Modeling the effects of electrical conductivity of the head on the induced electrical field in the brain during magnetic stimulation; Clinical Neurophysiology; vol. 114; pp. 2204-2209; 2004.

Davey et al.; Prediction of magnetically induced electric fields in biologic tissue; IEEE Transactions on Biomedical Engineering; vol. 38; pp. 418-422; 1991.

Davey et al.; Suppressing the surface field during transcranial magnetic stimulation; IEEE Transactions on Biomedical Engineering; vol. 53; No. 2; Feb. 2006; pp. 190-194.

DeRidder et al.; Transcranial magnetic stimulation for tinnitus: influence of tinnitus duration on stimulation parameter choice and maximal tinnitus suppression; Otol Neurotol.; vol. 26; No. 4; pp. 616-619; Jul. 2005.

Epstein et al.; Magnetic coil suppression of visual perception at an extracalcarine site; J. Clin. Neurophysiol; vol. 13; No. 3; pp. 247-252; May 1996.

George, Mark S.; Stimulating the brain; Scientific American; Sep. 2002; pp. 67-73.

Han et al.; Multichannel magnetic stimulation system design considering mutual couplings among the stimulation coils; IEEE Trans. on Biomedical Engineering; vol. 51; No. 5; pp. 812-817; May 2004.

Hemond et al.; Transcranial magnetic stimulation in neurology: What we have learned from randomized controlled studies; Neuromodulation: Technology at the Neural Interface; vol. 10; No. 4; pp. 333-344; 2007.

Hovey, C. et al.; The new guide to magnetic stimulation; The Magstim Company Ltd.; Carmarthenshire, United Kingdom; 2003.

Huang et al.; Theta Burst Stimulation of the Human Motor Cortex; Neuron; vol. 45; pp. 201-206; 2005.

Isenberg et al.; Low frequency rTMS stimulation of the right frontal cortex is as effective as high frequency rTMS stimulation of the left frontal cortex for antidepressant-free, treatment-resistant depressed patients; Ann Clin Psychiatry; vol. 17; No. 3; pp. 153-159; Jul.-Sep. 2005.

Lang et al.; How does transcranial DC stimulation of the primary motor cortex alter regional neuronal activity in the human brain?; Eur. J. Neurosci.; vol. 22; No. 2; pp. 495-504; Jul. 2005.

Lin et al.; Magnetic coil design considerations for functional magnetic stimulation; IEEE Trans. On Biomedical Eng.; vol. 47; No. 5; pp. 600-610; May 2000.

Magstim Website: http://www.magstim.com/magneticstimulators/magstimacc/12494.html (printed Mar. 23, 2010).

Martin et al.; Transcranial magnetic stimulation for treating depression; Cochrane Review; 2002 (In (eds.): The Cochrane Library. Oxford: Update Software: The Cochrane Library. Oxford: Update Software.).

Mayberg et al.; Deep brain stimulation for treatment-resistant depression; Neuron; vol. 45; pp. 651-660; 2005.

Nadeem et al.; Computation of electric and magnetic stimulation in human head using the 3-D impedance method; IEEE Trans on Biomedical Eng; vol. 50; No. 7; pp. 900-907; Jul. 2003.

Ohnishi et al.; rCBF changes elicited by rTMS over DLPFC in humans; Suppl Clin Neurophysiol.; vol. 57: pp. 715-720; 2004.

Paton et al.; Vascular-brain signaling in hypertension: role of angiotensin II and nitric oxide; Curr. Hypertens Rep; vol. 9; No. 3; pp. 242-247; Jun. 2007.

Roth et al.; A coil design for transcranial magnetic stimulation of adeep brain regions; J. Clin. Neurophysiology; vol. 19; No. 4; 2002; pp. 361-370.

Ruohonen et al.; Theory of Multichannel Magnetic Stimulation: Toward Functional Neuromuscular Rehabilitation; IEEE Transactions on Biomedical Engineering; vol. 46; No. 6; pp. 646-651; Jun. 1999.

Ruohonen, J.; Transcranial magnetic stimulation: modelling and new techniques; (doctoral dissertation); Helsinki Univ. of Tech.; Dept. of Eng. Physics and Mathematics; Espoo, Finland; 1998.

Ruohonen et al.; (Chapter 2); Magnetic stimulation in clinical neurophysiology; Second Ed.; Ed. Elsevier Inc.; pp. 17-30; 2005.

Ruohonen et al.; Focusing and targeting of magnetic brain stimulation using multiple coils; Medical & Biological Engineering and Computing; vol. 35; pp. 297-301; 1998.

Sackheim, H. A.; Commentary: Magnetic stimulation therapy and ECT; Convulsive Therapy; vol. 10; No. 4; 1994; pp. 255-285.

Sekino et al.; Comparison of current distributions in electroconvulsive therapy and transcranial magnetic stimulation; J. of Applied Physics; vol. 91; No. 10; pp. 8730-8732; May 15, 2002.

Speer et al.; Opposite effects of high and low frequency rTMS on regional brain activity in depressed patients; Biol. Psychiatry; vol. 48; No. 12; pp. 1133-1141; Dec. 15, 2000.

Takano et al.; Short-term modulation of regional excitability and blood flow in human motor cortex following rapid-rate transcranial magnetic stimulation; Neuroimage; vol. 23; No. 3; pp. 849-859; Nov. 2004.

Traad, Monique; A Quantitative Positioning Device for Transcranial Magnetic Stimulation; Engineering in Medicine and Biology Society; 1990; Proceedings of the 12th Annual Int'l Conf. of the IEEE; Philadelphia, PA; p. 2246; Nov. 1-4, 1990.

Ueno et al.; Localized stimulation of neural tissues in the brain by means of a paired configuration of time-varying magnetic fields; J. Appl. Phys.; vol. 64; No. 10; pp. 5862-5864; Nov. 15, 1988.

Vayssettes-Courchay et al.; Role of the nucleus tractus solitarii and the rostral depressive area in the sympatholytic effect of 8-hydroxy-2-(di-n-propylamino)tetralin in the cat; Eur. J. Pharmacol.; vol. 242; No. 1; pp. 37-45; Sep. 21, 1993.

Wagner et al.; Three-dimensional head model simulation of transcranial magnetic stimulation; IEEE Trans. on Biomedical Engineering; vol. 51; No. 9; pp. 1586-1598; Sep. 2004.

Waki et al.; Junctional adhesion molecule-1 is upregulated in spontaneously hypertensive rats: evidence for a prohypertensive role within the brain stem; Hypertension; vol. 49; No. 6; pp. 1321-1327; Jun. 2007.

Wasserman et al.; Therapeutic application of repetitive magnetic stimulation: a review; Clinical Neurophysiology; vol. 112; pp. 1367-1377; 2001.

Wasserman, E. M.; Risk and safety of repetitive transcranial magnetic stimulation: report and suggested guidelines from the International Workshop on the Safety of Repetitive Transcranial Magnetic Stimulation, Jun. 5-7, 1996; Electro-encephalography and Clinical Neurophysiology; vol. 108; pp. 1-16; 1998.

Xiao et al.; Magnetic Nanocomposite Paste: An Ideal High- $\mu$, k and Q Nanomaterial for Embedded Inductors in High Frequency Electronic Appls.; Proceedings of the 9th World Multiconference on Systemics, Cybernetics and Informatics; Orlando, FL; Jul. 10-13, 2005.

Partsch et al.; U.S. Appl. No. 12/669,882 entitled "Device and method for treating hypertension via non-invasive neuromodulation," filed Jan. 20, 2010.

Schneider et al.; U.S. Appl. No. 12/671,260 entitled "Gantry and switches for position-based triggering of tms pulses in moving coils," filed Jan. 29, 2010.

Schneider et al.; U.S. Appl. No. 12/701,395 entitled "Control and coordination of transcranial magnetic stimulation electromagnets for modulation of deep brain targets," filed Feb. 5, 2010.

Mishelevich et al.; U.S. Appl. No. 12/677,220 entitled "Focused magnetic fields," filed Mar. 9, 2010.

Blount et al.; The Influence of Thyroid and Thiouracil on Mice Exposed to Roentgen Radiation; Science; 109(2822); pp. 83-4; Jan. 28, 1949.

Buxton; Pharmacokinetics and Phamacodynamics; Goodman & Gilman's The Pharmacological Basis of Therapeutics (11th Ed.); McGraw-Hill, © 2006; pp. 1-23; pub. date Oct. 28, 2005.

George et al.; Prefrontal Repetitive Transcranial Magnetic stimulation (rTMS) Changes Relative Perfusion Locally and Remotely; Human Psychopharmacol Clin Exp; 14(3); pp. 161-170; Apr. 1999.

Kimeldorf et al.; The effect of exercise upon the lethality of roentgen rays for rats; Science; 112(2902); pp. 175-176; Aug. 1950.

Lemaire et al.; Influence of blood components on the tissue uptake indices of cyclosporin in rats; J Pharmacol Exp Ther; 244(2); pp. 740-3; Feb. 1988.

Rubin et al.; Radiosensitivity and radioresistance of tumors; Clinical Radiation Pathology; WB Saunders; Ch. 24, pp. 894-933; Jun. 1968.

(56) References Cited

OTHER PUBLICATIONS

Rubin et al.; The Modification of Radiation Response; Clinical Radiation Pathology; WB Saunders; Ch. 26, pp. 973-1008; Jun. 1968.

Smith et al.; Effect of thyroid hormone on radiation lethality; Am J Physiol; 165(3); pp. 639-650; Jun. 1951.

Speer et al.; Opposite effects of high and low frequency rTMS on regional brain activity in depressed patients; Biol Psychiatry; 48(12); pp. 1133-1141; Dec. 15, 2000.

Ueno; Individual differences in radio sensitivity of mice correlated with their metabolic rate; Acta Radiol Ther Phys Biol; 10(4); pp. 427-432; Aug. 1971.

Mishelevich et al.; U.S. Appl. No. 12/679,960 entitled "Display of modeled magnetic fields," filed Mar. 25, 2010.

Mishelevich et al.; U.S. Appl. No. 12/680,749 entitled "Intra-session control of transcranial magnetic stimulation," filed Mar. 30, 2010.

Mishelevich et al.; U.S. Appl. No. 12/680,912 "Transcranial magnetic stimulation with protection of magnet-adjacent structures," filed Mar. 31, 2010.

Schneider et al.; U.S. Appl. No. 12/838,299 entitled "Transcranial magnetic stimulation field shaping," filed Jul. 16, 2010.

Schneider et al.; U.S. Appl. No. 12/912,650 entitled "Sub-motor-threshold stimulation of deep brain targets using transcranial magnetic stimulation," filed Oct. 26, 2010.

Bodo et al.; The role of multidrug transporters in drug availability, metabolism and toxicity; Toxicol Lett; pp. 140-141; Review; pp. 133-43; Apr. 11, 2003.

Wasan et al.; Lipid transfer protein I facilitated transfer of cyclosporine from low-to high-density lipoproteins is only partially dependent on its cholesteryl ester transfer activity; J Pharmacol Exp Ther; 284(2); pp. 599-605; Feb. 1998.

Schneider et al.; U.S. Appl. No. 13/808,806 entitled "Transcranial magnetic stimulation for altering susceptibility of tissue to pharmaceuticals and radiation," filed Apr. 23, 2013.

Mishelevich et al.; U.S. Appl. No. 14/247,087 entitled "Shaped coils for transcranial magnetic stimulation," filed Apr. 7, 2014.

\* cited by examiner

BINARY EFFECT TABLES FOR DIFFERENTIAL PULSE PATTERNS

Key:
1 = pulse at 100% MT
0 = no pulse
Total time period of T1 through T10 is 1 second (Tx duration .1 second each)
BINARY OUTCOMES: 3 Scenarious using 3 parallel coil arrays

All COILS IN FAST SYNCHRONY

| | T1 | T2 | T3 | T4 | T5 | T6 | T7 | T8 | T9 | T10 | Net Rate at Target |
|---|---|---|---|---|---|---|---|---|---|---|---|
| Coil/Array A and superficial cor | 1 | 1 | 1 | 1 | 1 | 1 | 1 | 1 | 1 | 1 | 10Hz |
| Coil/Array B and superficial cor | 1 | 1 | 1 | 1 | 1 | 1 | 1 | 1 | 1 | 1 | 10Hz |
| Coil/Array C and superficial cor | 1 | 1 | 1 | 1 | 1 | 1 | 1 | 1 | 1 | 1 | 10Hz |
| Mutual Deep Target | 1 | 1 | 1 | 1 | 1 | 1 | 1 | 1 | 1 | 1 | 10 Hz |

2 COILS FAST, 1 COIL SLOW

| | T1 | T2 | T3 | T4 | T5 | T6 | T7 | T8 | T9 | T10 | Net Rate at Target |
|---|---|---|---|---|---|---|---|---|---|---|---|
| Coil/Array A and superficial cor | 1 | 1 | 1 | 1 | 1 | 1 | 1 | 1 | 1 | 1 | 10Hz |
| Coil/Array B and superficial cor | 1 | 1 | 1 | 1 | 1 | 1 | 1 | 1 | 1 | 1 | 10Hz |
| Coil/Array C and superficial cor | 1 | 0 | 0 | 0 | 0 | 0 | 0 | 0 | 0 | 0 | 1 Hz |
| Mutual Deep Target | 1 | 0 | 0 | 0 | 0 | 0 | 0 | 0 | 0 | 0 | 1Hz |

2 COILS FAST, 1 COIL MEDIUM

| | T1 | T2 | T3 | T4 | T5 | T6 | T7 | T8 | T9 | T10 | Net Rate at Target |
|---|---|---|---|---|---|---|---|---|---|---|---|
| Coil/Array A and superficial cor | 1 | 1 | 1 | 1 | 1 | 1 | 1 | 1 | 1 | 1 | 10Hz |
| Coil/Array B and superficial cor | 1 | 0 | 1 | 0 | 1 | 0 | 1 | 0 | 1 | 1 | 10Hz |
| Coil/Array C and superficial cor | 1 | 0 | 1 | 0 | 1 | 0 | 1 | 0 | 1 | 0 | 5 Hz |
| Mutual Deep Target | 1 | 0 | 1 | 0 | 1 | 0 | 1 | 0 | 1 | 0 | 5 Hz |

FIG. 6

DTDT= distance to deep target in cm, measured from bottom of cortical sulci
FF= falloff factor in %/cm
Less that 100% corresponds with NO ACTION POTENTIAL
100% or greater corresponds with ACTION POTENTIAL

STIMULATION CALCULATION TABLE: DISTANCE AND PERCENT POWER METHOD

| | DTDT | FF | T1 | T2 | T3 | T4 | T5 | T6 | T7 | T8 | T9 | T10 |
|---|---|---|---|---|---|---|---|---|---|---|---|---|
| Coil/Array A and superficial cortex beneath | 2.5 | 0.50 | 65% | 110% | 110% | 110% | 110% | 110% | 110% | 110% | 110% | 65% |
| Coil/Array B and superficial cortex beneath | 0.5 | 0.50 | 65% | 65% | 65% | 65% | 65% | 65% | 65% | 65% | 65% | 65% |
| Coil/Array C and superficial cortex beneath | 0.5 | 0.50 | 65% | 65% | 65% | 65% | 0% | 65% | 65% | 65% | 65% | 65% |
| Coil/Array D and superficial cortex beneath | 2.5 | 0.50 | 65% | 65% | 65% | 65% | 65% | 65% | 65% | 65% | 65% | 65% |
| Mutual Deep Target | | | 115% | 123% | 123% | 123% | 77% | 123% | 123% | 123% | 123% | 115% |

Percent power at "Mutual Deep Target" is the percent of target activation threshold or percent motor threshold.
Percent power shown at "Mutual Deep Target" calculated at each $T_n$ as:
$(FF^{DTDT} \times \%\ Power\ at\ T_n)_{Coil\ A} + (FF^{DTDT} \times \%\ Power\ at\ T_n)_{Coil\ B} + (FF^{DTDT} \times \%\ Power\ at\ T_n)_{Coil\ C} + (FF^{DTDT} \times \%\ Power\ at\ T_n)_{Coil\ D}$

FIG. 8

FIRING PATTERNS FOR DEEP BRAIN TRANSCRANIAL MAGNETIC STIMULATION

CROSS REFERENCE TO RELATED APPLICATIONS

This application claims priority to the following applications: U.S. Provisional Patent Application Ser. No. 60/956,920, filed on Aug. 20, 2007, titled "FIRING PATTERNS FOR DEEP BRAIN TRANSCRANIAL MAGNETIC STIMULATION."; U.S. Provisional Patent Application Ser. No. 60/970,958, filed on Sep. 9, 2007, titled "PULSING MULTIPLE INDEPENDENTLY TRIGGERED ELECTROMAGNETS FROM ONE OR MORE ENERGY SOURCES."; and U.S. Provisional Patent Application Ser. No. 61/077,488, filed on Jul. 2, 2008, titled "DIFFERENTIAL PULSE PATTERNS IN PARALLEL STIMULATION ARRAYS." Each of these applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

The devices and methods described herein relate generally to the triggering of electromagnets used for Transcranial Magnetic Stimulation.

BACKGROUND OF THE INVENTION

Transcranial Magnetic Stimulation (TMS) of the brain has been employed in a limited way to treat depression refractory to the administration of drugs. The number of treatable conditions may significantly increase as the depth of the target increases. Systems for targeting neural structures at depth (e.g., Schneider and Mishelevich, U.S. patent application Ser. No. 10/821,807, now U.S. Pat. No. 7,520,848, and Mishelevich and Schneider, U.S. patent application Ser. No. 11/429,504), now U.S. Pat. No. 8,052,591 may include multiple electromagnets, the firing of which must be coordinated. TMS stimulation of deep targets would potentially permit treatment of a variety of conditions such as chronic pain, addiction, obesity, depression, Alzheimer's disease, and Parkinson's disease. Conventional rTMS (repetitive transcranial magnetic stimulation) is capable of effectively stimulating only the outer cortical layer of the brain, and treats depression indirectly, by stimulating neural pathways that run from the prefrontal cortical surface to the cingulate gyrus, rather than hitting the target directly. It is preferable to stimulate deep structures such as the cingulate gyrus directly, but when targeting deep neural structures with rTMS, care must be taken to avoid over-stimulating superficial structures to eliminate undesired side effects such as seizures or producing unintended neural-stimulation results. It is thus necessary to avoid having too many successive pulses from the same electromagnet passing through such superficial structures while targeting the deep structure.

To effectively elicit an action potential in a neural structure, adequate stimulation must be received in a time period which is less than the minimum time (usually expressed as chronaxie) that it takes the target neural membrane to re-polarize. Otherwise threshold for generating an action potential will not be achieved. With respect to another time scale, for a given neural structure, stimulating pulses must be received within a maximum effective time interval such that the effect of the generated action potentials is additive. Neural elements are typically highly interconnected and the actual final target element to be stimulated will receive inputs from multiple sources The pulse-rate frequency from any given electromagnet location is preferably limited, typically to a rate of less than 50 pulses per second (i.e., 50 Hz). While limiting the frequency from a single stimulating location will protect structures superficial to the deeper target, it may be impossible to effectively stimulate a deep target because of the rapid fall off of the magnetic field (roughly $1/(distance)^2$ at short distances). Thus, different trajectories must be stimulated in turn. We have previously suggested accomplishing this by either moving the electromagnets, as is described in Schneider and Mishelevich, U.S. patent application Ser. No. 10/821,807 ("Robotic apparatus for targeting and producing deep, focused transcranial magnetic stimulation") or by sequentially firing electromagnets located at distributed locations. The approach of this latter case may avoid over-stimulating superficial neural structures at a single location and causing seizures or other undesired impacts, but to be successful, the pulsed magnetic fields must reach the target at a higher effective rate of stimulation than the pulsed magnetic fields hitting superficial tissue. The coordination of the orientation, timing, frequencies and power levels for controlling multiple magnets to stimulate one or more targets, and particularly deep tissue targets is a difficult task that has not yet been effectively accomplished. Described herein are methods, devices and systems for accomplishing this.

Furthermore, different tissues may have differing requirements in terms of the amount of function augmentation or suppression that they require, or that they can tolerate. For example, when seeking to suppress the activity of a remote target using slow rate rTMS delivered from multiple intersecting pathways, one or more intermediate tissues may be inadvertently suppressed in the process, when, in fact, such tissue(s) require functional augmentation.

For example, Isenberg et al., and others, have shown that either fast rate (e.g., 10 Hz) rTMS applied to the left dorsolateral prefrontal cortex (LDLPFC) or slow rate rTMS (e.g., 1 Hz) applied to the right dorsolateral prefrontal cortex (RDLPFC), are effective treatments for depression. Published studies have involved treating either of those two targets. The practical limitations of currently available equipment prevent the alternative or concurrent slow right and fast left treatment. These limitations stem from logistical difficulties in positioning TMS coils, and applying selected pulse parameters at the correct positions.

Arrays of multiple magnetic coils have been proposed. For example, Ruohonen et al. (1998) modeled in software an array of small adjacent magnets intended to stimulate the outer cortical surface of the brain. While power requirements are calculated in this study, no specific means for delivering or switching that power are disclosed. Ruohonen et al. (1999) modeled in software a multi-coil array for the purpose of limb rehabilitation. Again, no specific means for switching or delivering power to the appropriate coil were described. Instead, "the multichannel design allows the stimulus to be moved without moving the coils. This is accomplished by individually adjusting the strength and direction of the current in each coil." Han et al. (2004) proposed a multiple coil array, but they also had no particular strategy for powering the coils other than turning them on simultaneously, and describes, "[i]n the multichannel magnetic stimulation, it is assumed that the predetermined optimal currents are fed in-phase to the coils. Therefore, all the channels are generally ON state when a stimulation pulse is applied to the subject."

Thus, there is a need for appropriately controlling the stimulation from magnets so that the stimulation can be focused on deep tissue without creating undesired stimulation or inhibition effects in tissue superficial to the deep target. Furthermore, if effects are to be induced upon the intervening neural structures, those effects should be calculated, controllable, desirable effects. The control of the system must allow powering of the array of magnets by tapping the stored charge from one or more sources, and delivering them precisely, under the appropriate circumstances to each coil, individually. There is also a need for a system by which the pulse rate, power and pattern of stimuli delivered through intermediately juxtaposed brain tissue may be different in the different coils of the array, thereby better suiting the characteristics and therapeutic needs of that intermediate brain tissue as well as that of the principal target. Depending on the number of electromagnets, the capacity of the power sources, and other factors, it may be more appropriate to supply power for the triggering of the electromagnets from either a single power source or multiple power sources. Systems, devices and methods to address these needs, as well as others, are described in greater detail below.

SUMMARY OF THE INVENTION

Described herein are methods, devices and systems for controlling the firing of electromagnets located at different positions to stimulate at least one brain region, including deep brain regions. The firing may be performed at fixed, random, or mixed fixed and random intervals, and/or at different pulse rates. In general, the methods described herein include methods of focusing stimulating from multiple magnets on one or more brain region so that energy from the magnets sums in a desired brain region to trigger firing of neurons (e.g., action potentials) in the target brain regions without triggering firing in adjacent (and particularly superficially located) brain regions. The methods further include controlling the timing, rate, and power of each magnet in an array of magnets to achieve transcranial magnetic stimulation so that energy applied by the magnets to non-target regions is below a threshold for stimulation and energy applied to target regions is above the threshold. Furthermore, the rate of stimulation (e.g., the rate that action potentials are evoked) in target regions may be controlled to modulate the effects of stimulation of a target region.

In one embodiment, one or more pulses can be generated (e.g., 3, 2, 2, 1, 5 pulses etc.) at one location before moving on to the next. Alternatively, some or all the pulses can be concurrently fired from two or more locations. Instead of whole trains of pulses stimulating a given volume of superficial tissue, relatively few pulses per a given period of time may be fired from locations close to, and potentially stimulate the superficial tissues, but the magnetic pulses reaching the deep target location from a plurality of magnets may combine to form a pulse train that activates the desired volume of target tissue. The plurality of electromagnets referred to herein may be in fixed positions or may be mobile (as in Schneider and Mishelevich, U.S. patent application Ser. No. 10/821,807). The net effect at the target location is due to combined elements of temporal and spatial summation.

This approach may also be used to take advantage of the individual properties of different brain regions, permitting each region to be stimulated with the pulse sequence that maximally contributes to the overall intended effect of the treatment. For example, adverse effects may result if pulse rates exceed 3 Hz when the pulse trajectory passes through the right dorsolateral prefrontal cortex on the way to a cingulate target. Consequently, it may benefit the overall treatment strategy to limit the rate of pulses passing through the right dorsolateral prefrontal cortex, even though a faster pulse rate would help the temporal summation effect.

By coordinating the activity of a plurality of electromagnets, each of which must receive a certain amount of pulsed electrical charge at specific times with respect to one another, the devices, methods and systems described herein may control the stimulation of one or more brain regions, including regions previously thought to be too deep for controlled transcranial magnetic stimulation. This process may occur in configurations in which the charge pulses received by these electromagnets are simultaneous, and when the charge delivery among these coils is not simultaneous.

In one variation, a single power source has an output directed to multiple electromagnets by controlling which driver is gated to conduct to a given electromagnet via a distributor element controlled by a stimulation controller. In another variation, multiple power sources (for example, one for each electromagnet) are each controlled via an associated driver. The gating of the drivers is determined by a distributor element controlled by a stimulation controller. Single power source and multiple power source configurations can be mixed in a single system.

These methods, systems and devices may also allow a neuromodulation-produced energy source to simultaneously deliver different effects to different neural tissues. For example, multiple stimulation trajectories or multiple stimulation sources (e.g., TMS coils) may be controlled to achieve targeted stimulation. Each of these sources may be capable of independent function. The cumulative effect of the multiple sources at the intersection of their paths, as well as the independent effects of each source in proximal tissue, are calculated and controlled by the system described.

BRIEF DESCRIPTION OF THE DRAWINGS

FIG. 6 is a table that illustrates three variations of ways in which the coils such as those shown in FIG. 5 may be activated in order to achieve a desired effect, including three threshold-based (action-potential-elicited versus no-action-potential-elicited) calculations.

FIG. 8 is a table that tallies the effect of different pulse patterns in the coils shown in FIGS. 7A and 7B in a manner that considers distance from each coil, and the strength of the magnetic pulses (measured continuously rather than as a binary variable), and the resultant effect upon the target structure relative to interposed superficial structures.

DETAILED DESCRIPTION OF THE INVENTION

The Transcranial Magnetic Stimulation (TMS) methods, devices and systems described herein are capable of triggering action potential (including specified patterns of action potentials) in one or more target brain regions without triggering action potentials in nearby non-target regions, including regions that are superficial (e.g., between the target region and the external magnets(s) stimulating the brain). These TMS systems may support a variety of action potential firing patterns by controlling the pulsing of multiple, independently triggerable, electromagnets from one or more energy sources. The system may also monitor or control the one or more power supplies so that there is sufficient capacity from the power supplies so when a given pulse is triggered, adequate power is available to deliver a stimulus from each electromagnet as needed to trigger the desired action potentials from the target brain region.

Figure 1:
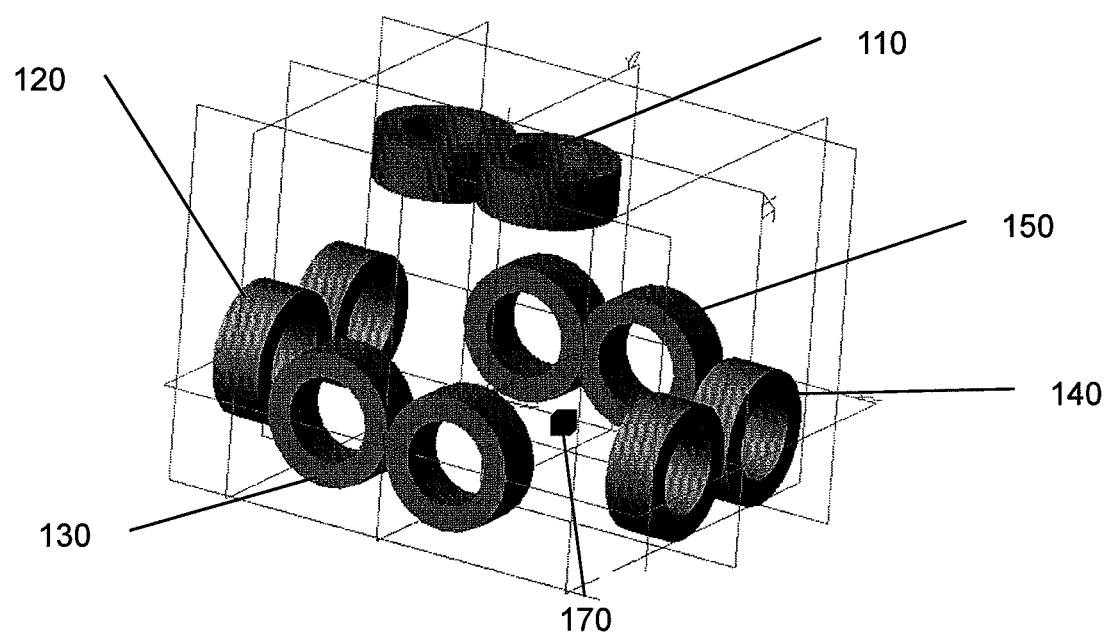
FIG. 1 shows five coil-pair sets of electromagnets.

FIG. 1 illustrates a configuration incorporating five electromagnets 110, 120, 130, 140, and 150 which may be used as part of a TMS system as described herein. The electromagnets need not be of equal size, and do not have to be in a uniform relationship to each other. The electromagnets may move as a group (say on a gantry or robotic arm) and/or in relationship to each other over time. For example, the electromagnets may be moved during stimulation (TMS) or they may be fixed during stimulation. In FIG. 1, a target neural (brain) tissue region 170 is illustrated. This region need not be equidistant from the electromagnets. Two or more electromagnets must be included; in the description of the embodiments illustrated in FIGS. 2 and 3, four electromagnets are incorporated.

In general, the devices and systems described herein may be used to stimulate one or more regions of the brain. As used herein "stimulation" of a brain region may refer to the eliciting of one or more (or a series of) action potentials from the brain region. Deep brain regions in particular may be stimulated with these devices and methods. As used herein the phrase "deep brain regions" may refer to cortical and sub-cortical brain regions, or just sub-cortical brain regions (e.g., regions below the subject's cortex). In some variations, multiple brain regions (including a cortical and a sub-cortical brain region, two or more sub-cortical regions, etc.) may be stimulated. For example, a complex pulse rhythm such as the "theta" pattern (Huang et al., 2005) on one region of the brain may facilitate TMS-induced neuromodulation effects in another part of the brain. Thus, the systems described herein may be used to simultaneously stimulate such a pattern in one region while simultaneously stimulating another region.

In order to stimulate one or more brain regions, the TMS systems described herein control the plurality of electromagnets to trigger pulses of an appropriate strength, duration and frequency (including complex patterns of stimulation), at each of the plurality of electromagnets so that only target brain region(s) are activated. Triggering of pulses can be done mechanically (e.g., through notches in a cam) or electronically using a built-in fixed, random, or mixed pattern or such patterns can be generated under computer control.

In general, the system may generate appropriate firing patterns for each of the plurality of electromagnets in the system. The "firing pattern" may refer to the duration of a pulse, the frequency of the pulse, and the intensity (strength) of the pulse (e.g., the current/voltage applied to generate the pulse). The system typically controls and coordinates the firing patterns of all of the electromagnets. For example, the electromagnets may be fired in a sequential order (e.g., first electromagnet, second electromagnet, third electromagnet, etc.) or in some other order (including random or pseudo-random). An example of a sequential firing pattern is shown in Table 1 and of a random firing is shown in Table 2, below. In Table 1, electromagnets at five different locations, A through E represented in the table columns, are triggered sequentially as the process steps through times 1 through 10 represented in the table rows. The objective is to minimize the number of pulses received by tissues close to a given electromagnet to avoid undesirable side effects while maximizing the number of pulses stimulating the target. Each pulse must be of sufficient duration so that the neural membrane will not re-polarize. For example, the chronaxie of a typical cortical neuron is 450 microseconds. The electromagnets are physically distributed such that tissues close to one electromagnet location (e.g., location "A") will be little impacted by pulses from a different location (location "B"). In Table 1, for location A, pulses may be triggered at time steps 1 and 6, so at the end of time step 10, two pulses have passed through neural tissue from the electromagnet at location A. The same effect will be true for electromagnets at locations B through E. The common target, however will have received a pulse at each time step, albeit at a somewhat lower magnitude because it is further away than tissues close to the electromagnets at locations A through E. As demonstrated, at the end of 10 time steps, tissues near the individual electromagnet locations A through E will have received only two pulses where the target deep location will have received ten pulses.

TABLE 1

SEQUENTIAL FIRING PATTERN

| | LOCATION | | | | | |
|---|---|---|---|---|---|---|
| TIME | A | B | C | D | E | TARGET |
| 1 | 1 | | | | | 1 |
| 2 | | 1 | | | | 1 |
| 3 | | | 1 | | | 1 |
| 4 | | | | 1 | | 1 |
| 5 | | | | | 1 | 1 |
| 6 | 1 | | | | | 1 |
| 7 | | 1 | | | | 1 |
| 8 | | | 1 | | | 1 |
| 9 | | | | 1 | | 1 |
| 10 | | | | | 1 | 1 |
| CUM TOTALS | 2 | 2 | 2 | 2 | 2 | 10 |

The TMS systems described herein may include control logic that coordinates the firing pattern, as well as the timing, strength and duration of the pulses applied by the electromagnets. This control logic (which may be part of a controller, and may be hardware, software, or both) may receive inputs regarding the subject's target anatomy (e.g., the location of one or more targets relative to the electromagnets), as well as information regarding the status of the power supply(s) indicating available power. Finally, inputs such as the desired rate of evoked action potentials for a target region may also be included. Additional inputs may be used as well. These inputs may help the control logic to determine the stimulation at each of the electromagnets, including what the firing pattern should be.

An example of a random firing pattern is demonstrated in Table 2. In this example, the same net number of pulses is delivered to tissues close to the electromagnets at locations A through E while the deep target receives 10 pulses, similar to the pattern shown in Table 1. Sequential and random firing patterns can be mixed to produce the same results, and more than one pulse can be triggered at a given time step before moving on to the next time step. Some or all the pulses can be simultaneously fired from two or more locations.

TABLE 2

RANDOM FIRING PATTERN

| TIME | LOCATION | | | | | TARGET |
|---|---|---|---|---|---|---|
| | A | B | C | D | E | |
| 1 | | 1 | | | | 1 |
| 2 | | | 1 | | | 1 |
| 3 | 1 | | | | | 1 |
| 4 | | | | 1 | | 1 |
| 5 | | | | 1 | | 1 |
| 6 | | 1 | | | | 1 |
| 7 | | | | | 1 | 1 |
| 8 | 1 | | | | | 1 |
| 9 | | 1 | | | | 1 |
| 10 | | | | | 1 | 1 |
| CUM TOTALS | 2 | 3 | 1 | 2 | 2 | 10 |

The time interval between time steps 1 through n may be tailored to deliver the pulses at a rate that is faster than the interval at which the target neural elements (neurons of the target brain region) will re-polarize; at this faster rate, the threshold for the target neural elements will be exceeded and desired effective stimulation may occur, triggering an action potential. The firing rate of the individual electromagnets at locations A through n (and thus the combined pulse rate that will be delivered at the target location) depends on the number of those individual electromagnets. For example, to achieve a pulse rate at the target to be 1000 Hz, if there are five individual electromagnets (e.g., A through E), this can be achieved by stimulating those five electromagnets at an effective rate of about 200 Hz each. If there are three only individual electromagnets (e.g., A through C), this can be achieved by stimulating those five electromagnets at an effective rate about 333 Hz each. All of the electromagnets need not be fired at the same frequency to achieve the effect. For example to get a pulse rate of 1000 Hz at the target, two of three electromagnets could have an effective firing rate of 400 Hz and the third could have an effective firing rate of 200 Hz. It is also not necessary that the electromagnets be of uniform type or size. In any situation involving random firing, the time interval can vary as well as the firing sequence.

The system may also control the firing pattern in order to achieve a desired rate of stimulation of the target tissue (e.g., a rate of action potential firing). For example, the system may control the electromagnets so that high pulse rates (e.g., 1000 Hz) may be achieved for only a fraction of a second, for example over 5 successive pulses, closely spaced, one from each of 5 electromagnets, followed by a pause. In such a case, the "1000 Hz" pulse burst may be experienced by neurons as a single stimulation. Provided that a sufficient period of wait (e.g., 0.2 seconds) separates the rapid (e.g. 1000 Hz) multi-electromagnet bursts, the net effect experienced by a deep target tissue will of a much slower pace, for example, between 5-50 Hz. The same principle may be applied to the production of temporally summated multi-electromagnet bursts in the production of slow-rate or fast-rate rTMS. For example, even if 5 electromagnet are discharged once each at a 1000 Hz rate, so long as about 1 second separates the overlapping bursts (e.g., the bursts summed in the target tissue), the effective pulse rate and safety profile experienced by a given brain part will be just short of 1 Hz. Thus, by firing each electromagnet once, each in rapid (e.g., 1000 Hz) succession (a "burst"), but then waiting 0.2 seconds to 1 second between bursts, we can get temporal summation and the safety of normal rTMS rates.

The TMS systems described herein may therefore attend to the overall stimulation pattern while controlling each electromagnet (or groups of electromagnets) individual firing rates, durations and strengths. In general, the stimulation of target tissue results from the temporal and spatial summation of the effect of the applied electromagnetic field at the target tissue. Thus, the system determines the appropriate firing pattern for all of the electromagnets as well as the individual firing (strength, duration and rate) for each electromagnet so that the firing of each electromagnet results in a sub-threshold energy for the non-target tissue, but the focused energy on the target tissue is above-threshold. As indicated, controlling the power applied by the system is one part of this control. In general, each electromagnet may be powered by a single power source, multiple power sources, or one power source may be used to power multiple electromagnets.

Figure 2:
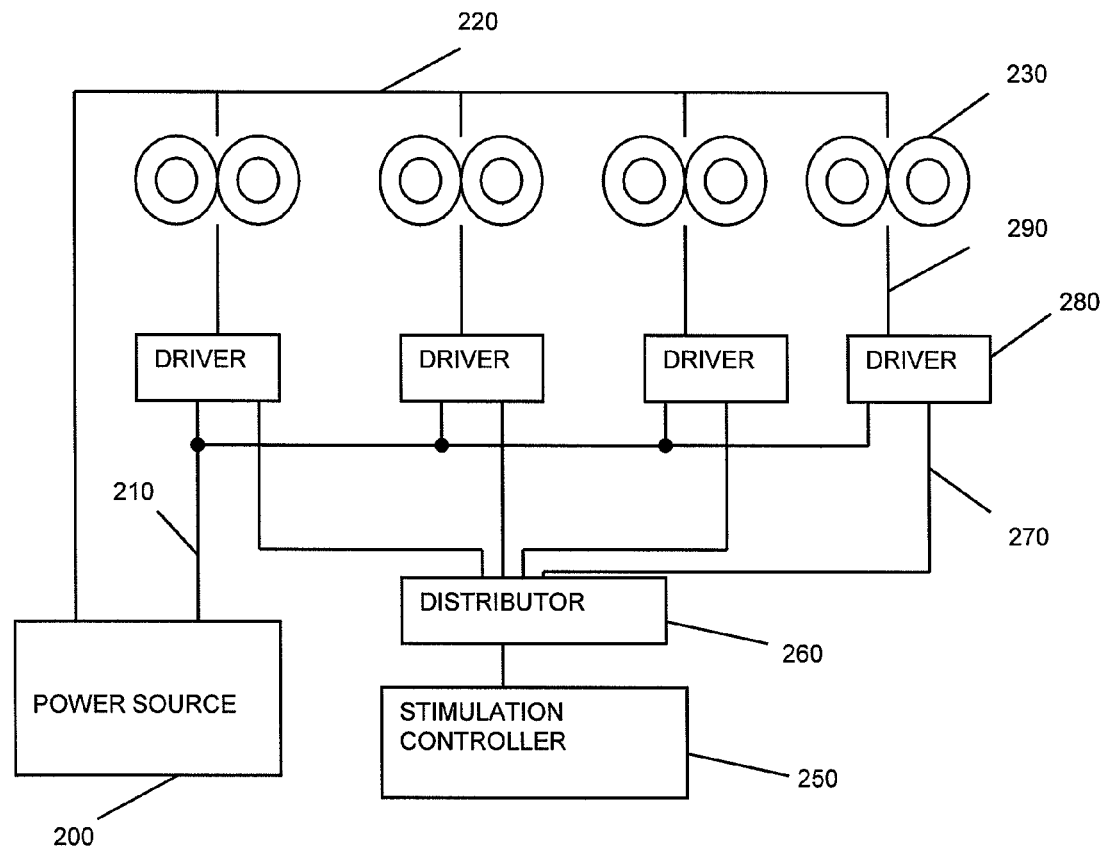
FIG. 2 illustrates one embodiment of a system for stimulating neuronal tissue deep within a subject's brain in which the power for the electromagnets is provided by a single energy source.

FIG. 2 illustrates an embodiment of a TMS system in which power for the electromagnets is provided by a single energy source. One output of power source 200 is provided in common via connection 220 to all of the electromagnets 230. While four electromagnets 230 are shown in the figure, any number feasible in the applied geometry can be powered. The firing of the individual electromagnets is determined by stimulation controller 250, which activates distributor 260 to select the appropriate driver 280 which when selected at the given time delivers power via connection 210 from power source 200 to the associated electromagnet 230 via connection 290.

Figure 3:
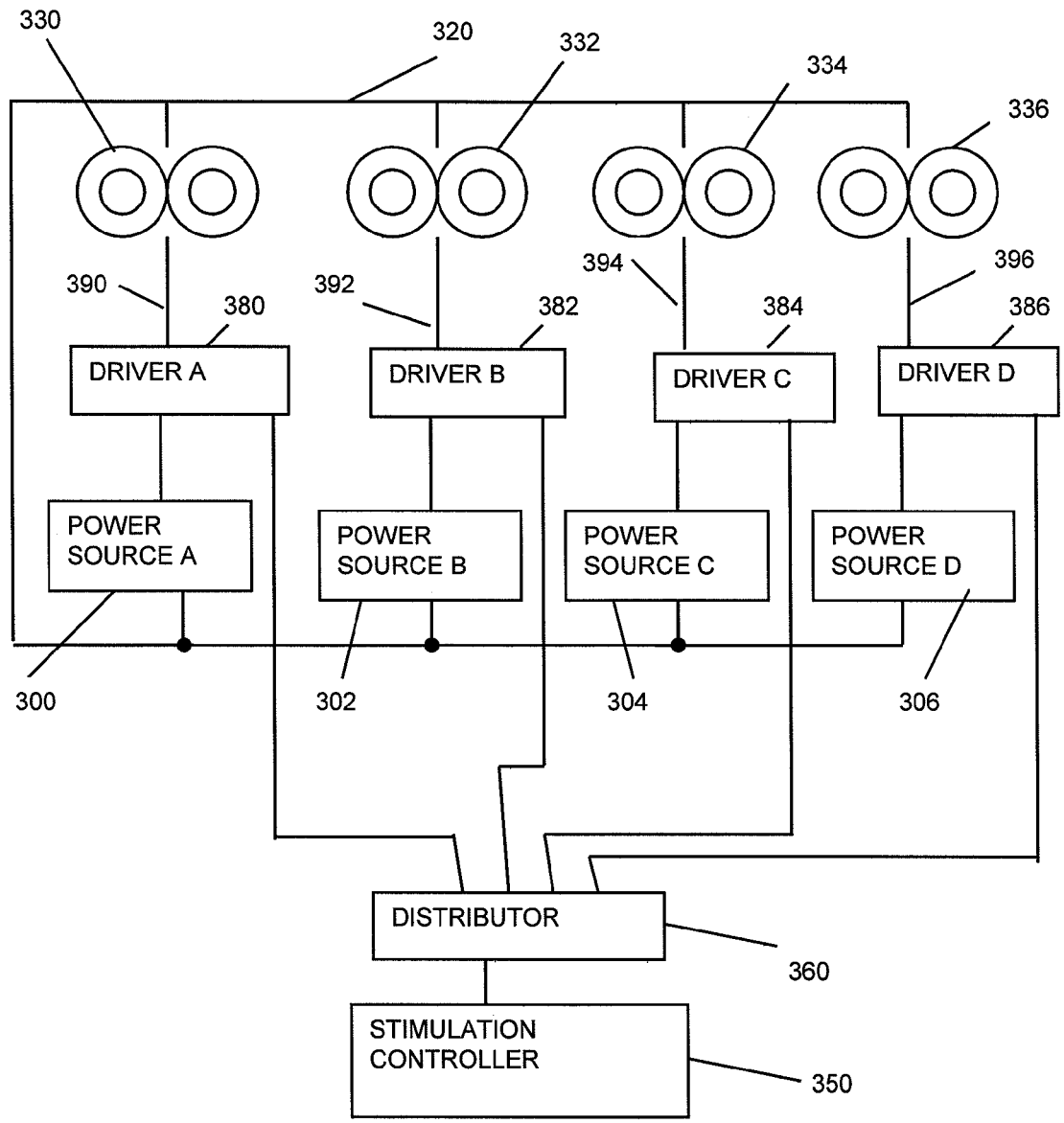
FIG. 3 illustrates another embodiment of a system for stimulating neuronal tissue deep within a subject's brain in which the power for the electromagnets is provided by multiple individual energy sources.

FIG. 3 illustrates an embodiment in which power for the electromagnets is provided by individual power sources. One output of all the power sources (e.g., power sources A through D) 300, 302, 304, 306 is provided in common by connection 320 to all the electromagnets 330, 332, 334, 336. Although four electromagnets 330, 332, 334, 336 are shown in the figure, any number of electromagnets feasible to the applied geometry can be powered. The firing of the individual electromagnets in this example determined by stimulation controller 350, which activates distributor 360 to select the appropriate driver (e.g., drivers A through D) 380, 382, 384, or 386 which when selected at the given time delivers power via associated connection 390, 392, 394 or 396 from respective power source 300, 302, 304 or 306 to the associated electromagnet 330, 332, 334 or 336. The controller 350 may run the control logic coordinating the stimulation of the target while avoiding stimulation of non-target regions.

In either variation illustrated in FIG. 2 and FIG. 3, more than a single electromagnet can be pulsed simultaneously, so long as the power source (e.g., FIG. 2) or power sources (e.g., FIG. 3) have sufficient capacity. As mentioned, the control logic may determine the appropriate output based on the available capacity of the power source(s). This capacity may be monitored directly (e.g., by one or more inputs), based on specification, or based on calculation or estimate.

Figure 4:
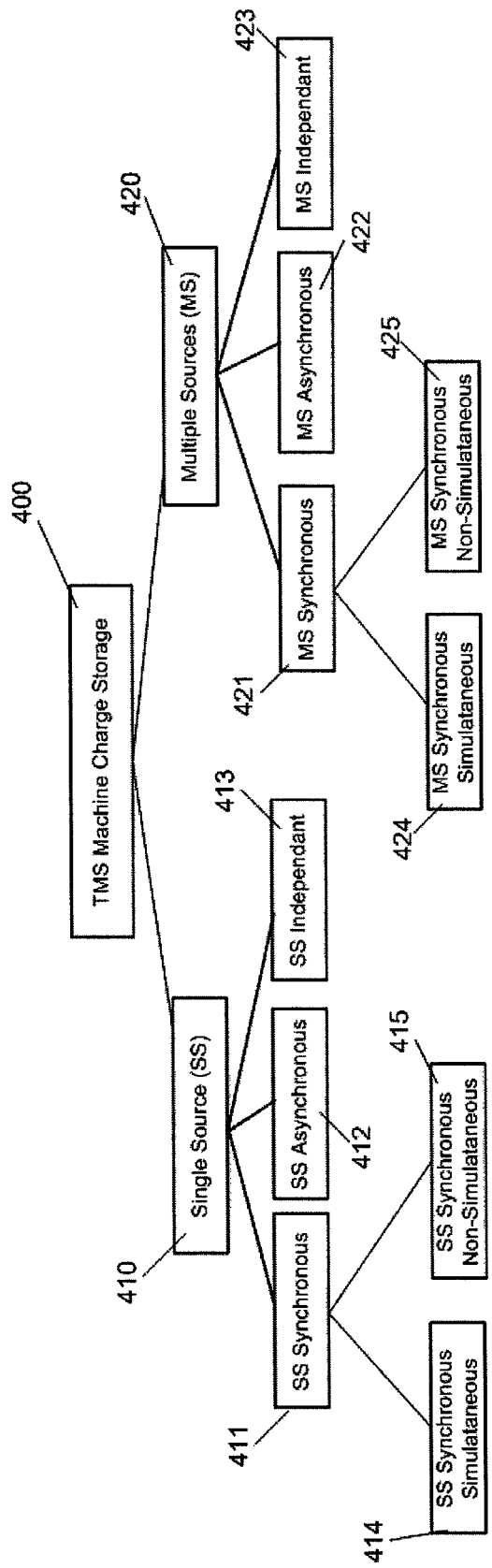
FIG. 4 illustrates various forms of control that can be provided for the plurality of coils.

FIG. 4 illustrates various examples of control of the firing pattern and excitation of the electromagnets (coils) that can be provided for the plurality of coils in accordance with the present invention as above described. Electromagnet charge storage 400 may be divided into Single Source methods 410 and Multiple Source methods 420. Single Source methods 410 may be subdivided into categories, as shown in FIG. 4. Single Source Synchronous pulses 411 are used in order to make the single power source deliver charge to each of a plurality of coils at timings that bear a fixed relationship to one another. Examples may include simultaneous (414) pulses, and non-simultaneous (415) pulses. Single Source Asynchronous pulses 412 describe those in which charge from a single charge storage device is metered to a plurality of coils in a manner such that each coil fires based upon a signal other than a time scale shared by the coils. The initiation of asynchronous firing may in include, for example, sensing that a series of pulses delivered by one coil has finished. Single Source Independent pulses 413 describe those in which the activity of one coil is not synchronized with, and does not influence the activity of another coil. Very large stored charge reservoirs are required to successfully use this approach.

Multiple Source methods (420) may also be subdivided into categories. Multiple Source Synchronous pulses 421 are used in order to make the single power source deliver charge to each of a plurality of coils at timings that bear a fixed relationship to one another. Examples may include simultaneous (424) pulses, and non-simultaneous (425) pulses. Multiple Source Asynchronous pulses 422 describe those in which charge from a single charge storage device is metered to a plurality of coils in a manner such that each coil fires based upon a signal other than a time scale shared by the coils. The initiation of asynchronous firing may in include, for example, sensing that a series of pulses delivered by one coil has finished. Multiple Source Independent pulses 423 describe those in which the activity of one coil is not synchronized with, and does not influence the activity of another coil. This may be more readily accomplished than with a single source, as power may be specifically allotted to the activity of any given coil.

Figure 5:
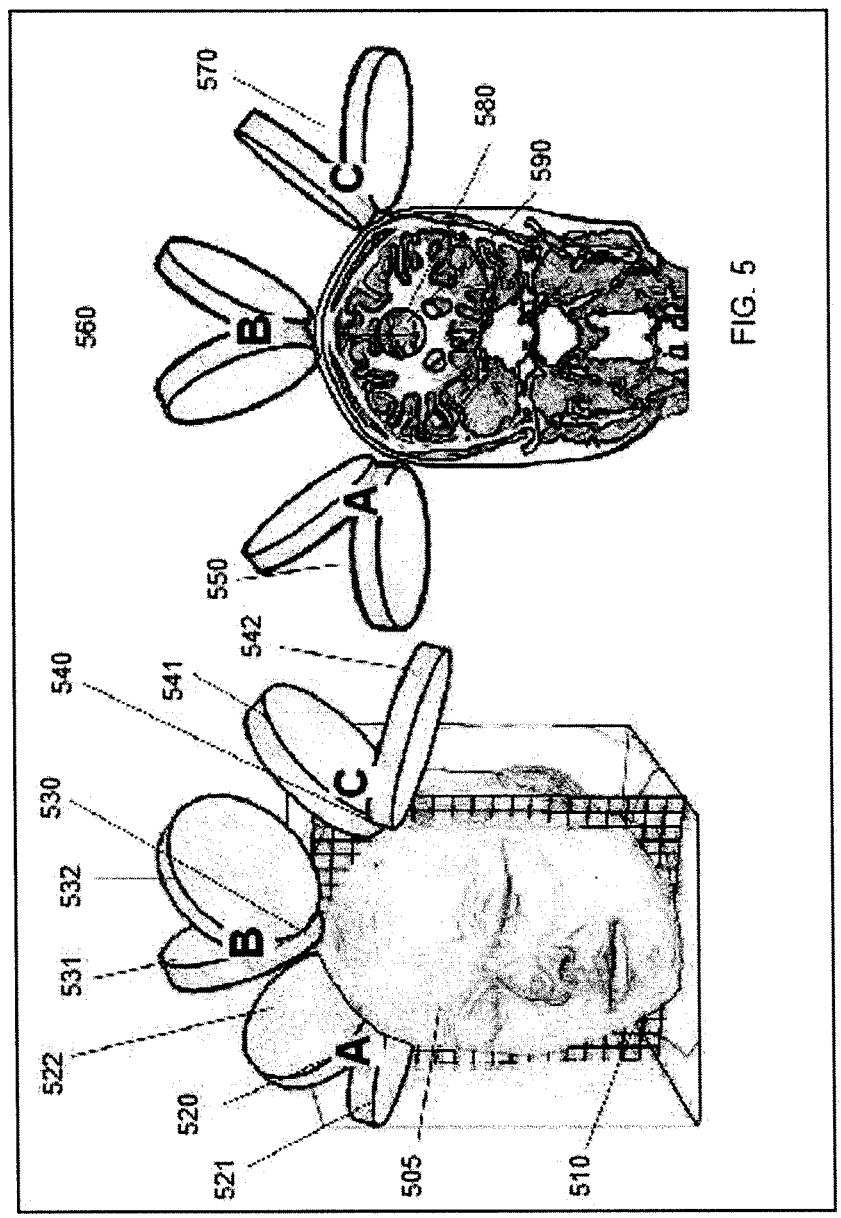
FIG. 5 shows an array of 3 energy sources around a patient's head, shown in frontal external view (left), and in cross section (right).

FIG. 5 shows an array of 3 (double) stimulator coils (referred to herein as three 'electromagnets') around a patient's head, in an image based in part on image data from Voxel-Man 3D Navigator. The head of the subject 505 is shown transected by plane 510. V-shaped double coil 520 (also designated as coil A or electromagnet A) is composed of circular coils 521 and 522, and bent at the center where the return path of the current in both coils is in the same direction. Similarly, V-shaped double coil 530 (also designated as coil B or electromagnet B) is composed of circular coils 531 and 532 joined at a bent center, and V-shaped double coil 540 (also designated as coil C or electromagnet C) is composed of circular coils 541 and 542, joined at a bent center. Within the subcortical (or "deep") target area 580 (in this example the left and right cingulum), there is targeted anatomy 590, in this example, cingulate fiber bundle 580. In another embodiment the electromagnets are not V-shaped, but traditional figure-8 double coils. In still another embodiment, not all of the axes across the faces of the electromagnets are oriented in the same direction.

It is assumed that the distance between the bottom of the nearest cortical sulcus and the underlying deep target is less than the distance between the physical coil centers. Under these conditions, the magnetic fields will summate at the deep target to a greater degree than at the cortical surface.

By pulsing one or more coils at a polarity that is same as that of an adjacent coil, magnetic flux reaching some locations may be augmented. Conversely, by pulsing one or more coils a polarity that is opposite that of an adjacent coil, magnetic flux reaching some locations may be neutralized. For example if Coil 560 is reverse-biased with respect to coils 550 and 570, respectively, the medial aspect of the field emitted by coils 550 and 570 may be largely cancelled. This effect may be controlled by the TMS system described herein, and may be helpful in focusing the target area.

For example, a TMS system as described herein may be used to generate a fast rTMS pulse rate to a peripheral brain region and slow pulse rate to a deep target region. This pattern of stimulation (and the resulting firing pattern and set of instructions for the electromagnet) may be particularly useful for reducing dorsal anterior cingulate metabolic rate while increasing motor cortex or prefrontal metabolic rate, such as in the context of a subject being treated for pain or OCD with depression. When the pulses are rapid but temporally staggered for a time interval that exceeds the chronaxie of the target, a rapid stimulation effect will be registered near each coil, but the target at the intersections of the energy path does not summate because of temporal staggering of the pulses from the periphery. By having some pulses (for example, 1 per second) from the periphery coincide temporally (or occur in rapid succession such that they fall within the chronaxie time of the deep target neurons), a slow rate at the deep target can be achieved even as the sites at the periphery achieve a fast stimulation rate.

In another example, it may be clinically desirable to have a slow rTMS pulse rate to peripheral brain and fast pulse rate to a deep target, at the intersection of the energy paths. For example, it may be desirable to decrease excessive prefrontal metabolism and increase dorsal anterior cingulate activity, for treating attention deficit hyperactivity disorder. The controller may receive the target information (identifying the location of the targets relative to the electromagnets), and may calculate, either before stimulation or on-the-fly, during stimulation, to achieve the desired effect. For example, pulses from each of the multiple sources may be delivered in a staggered fashion so as to make pulses in the periphery slow, and pulses at the intersection of the energy fast. By powering pulses at a rapid rate, but sub-threshold in power (e.g. 99% MT), interspersed with slow rate pulses of suprathreshold power (e.g. 120% MT), the target at the intersection of the energy paths center will experience rapid stimulation, while the locations beneath one or more coils will experience only slow-rate stimulation. Because rTMS pulses are quite brief (approx 0.1 to 0.3 ms in duration), there is an abundance of temporal "space" in between pulses of even a rapid train in which to deliver pulses in an asynchronous fashion, distributed between several different coils.

FIG. 6 shows a table illustrating three example of activation of electromagnets of a TMS system similar to that shown in FIG. 5, in order to achieve a desired effect, including three threshold-based (action-potential-elicited versus no-action-potential-elicited) calculations. In this table, the value of "1" means that an action potential is elicited, as the critical threshold has been exceeded. By contrast, "0" means that no action potential has occurred, as the critical threshold value of the cumulative effect has not been exceeded. T1 through T10 are sample times within an interval, which in this case are defined as 0.1 ms intervals. In alternative embodiments, T1-T10 may represent different time periods. They may or may not be spaced at regular time intervals. In each of the three tables, it is assumed that the distance between the bottom of the nearest cortical sulcus and the underlying deep target is less than the distance between the physical coil centers. Under these conditions, the magnetic fields will summate at the deep target to a greater degree than at the cortical surface. The assumptions behind what produces an adequate summation in each of these scenarios will be further explored below in the discussion of FIG. 8. Control logic (e.g., part of a controller) may be used to determine (e.g., calculate) this stimulation pattern, as well as the parameters of each stimulation provided by the individual electromagnets, including the powering of each electromagnet, necessary to achieve this stimulation pattern.

In the first of the three tables shown in FIG. 6, the top table shows a scenario in which pulses are delivered from each of Coil A, Coil B, and Coil C at each of the ten time intervals. Accordingly, the summated "mutual deep target" is stimulated to action potential at each pulse, for a net deep stimulation rate of 10 Hz. In this example, the deep target region (at the intersection of the pulses emitted by Coils A, B, and C) is stimulated, as is the more superficial cortical regions beneath Coils A, B and C.

In the second of the three tables shown in FIG. 6, Coils A and B are shown being pulsed at a fast 10 Hz rate, while Coil C is pulsed a slow 1 Hz rate, with a pulse only at T1. Because it is assumed that two coils at these spacing are too far from the mutual deep target to produce summation, the output at the mutual deep target is shown to be a "1", or action potential only at T1. Thus the net effect at the mutual deep target is 1 Hz stimulation, while the more superficial regions are stimulated at 10 Hz.

In the final of the three tables shown in FIG. 6, Coils A and B are shown being pulsed at a fast 10 Hz rate, while Coil C is pulsed a medium rate of 5 Hz, occurring at every other time interval. Because it is assumed that two coils at these spacing are too far from the mutual deep target to produce summation, the output at the mutual deep target is shown to be a "1", or action potential only at every other time interval. Thus the net effect at the mutual deep target is 5 Hz stimulation.

Of course, in FIG. 6, the stimulation at each of the cortical regions is indicated as "100% MT" (above threshold) for stimulation at those regions. "MT" refers to motor threshold, a standard (based on stimulation of motor cortex) for evoking a response via Transcranial Magnetic Stimulation; "100% MT" or greater (e.g., "115% MT") may result in an evoked action potential. The stimulation applied may be below threshold (<100% MT), while still summing to provide sufficient (at or above 100% MT) for the deeper brain regions. Thus, the cortical or regions superficial to the deep target may be un-stimulated so that they do not fire action potentials, while still stimulating the deeper region(s).

Figure 7A:
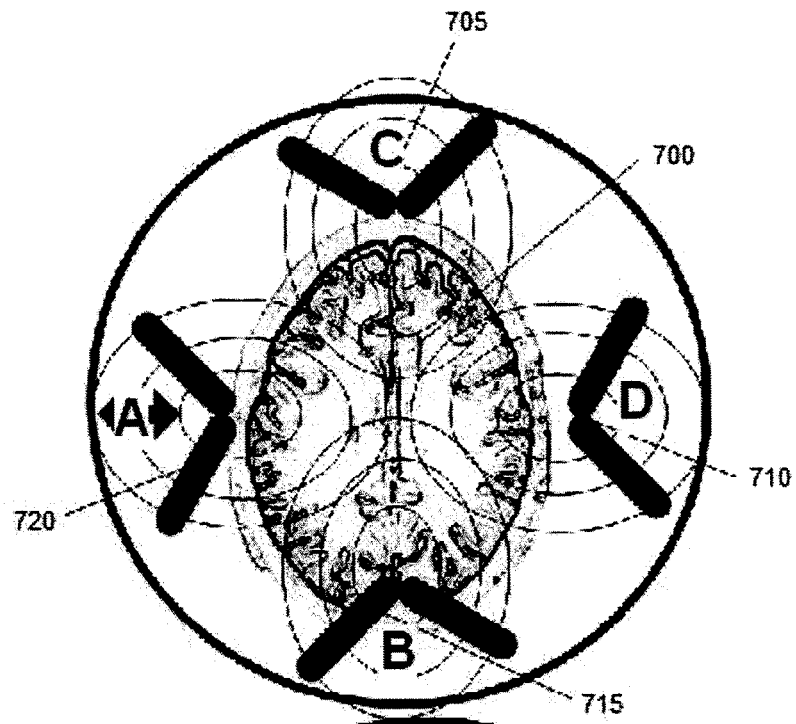
FIGS. 7A and 7B show two exemplary arrays of 4 (double) stimulator coils positioned around a patient's head.
Figure 7B:
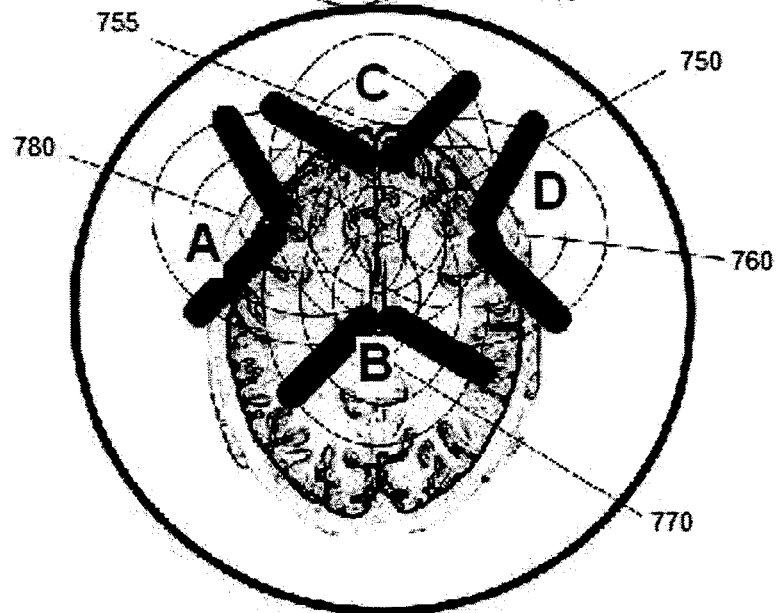

FIGS. 7A and 7B shows two different exemplary array configurations, each consisting of four double coils around a patient's head, and centered upon the same cingulate target illustrated as the mutual deep target in FIG. 5. The electromagnets may be movable during the TMS treatment, so that the position of the applied energy may be moved. Such a coil-moving device may be like that described in Schneider and Mishelevich, U.S. patent application Ser. No. 10/821,807. In other example, the TMS system may include stationary coil arrays. Stationary coils may be moved (repositioned) prior to treatment, or between treatment steps.

In FIG. 7A, the upper portion of the figure, coils 705, 710, 715 and 720 are in locations too distant from the dorsal anterior cingulate target 700 to effectively modulate its activity. However, by moving coils into a closer pattern as shown in the lower figure, FIG. 7B, effective use of the array becomes possible. In FIG. 7B, coils 755, 760, 770 and 780 have moved much closer together and closer to dorsal anterior cingulate target 750 in a 3D pattern overlaid upon a 2D axial slice. This configuration may also be achieved using three or more standard flat TMS coils, with their "flat planes" at right angles to one another, as described by the present inventors in U.S. patent application Ser. No. 11/429,504.

FIG. 8 is a table that tallies (simulates) the effect of different pulse patterns of the coils shown in FIG. 7B in a manner that considers distance from each coil, and the strength of the magnetic pulses (measured continuously rather than as a binary variable), and the resultant effect upon the target structure relative to interposed superficial structures. The distance to the target for a given electromagnet is DTDT which is the "Distance to The Deep Target" in centimeters measured from the bottom of the cortical sulcus through which the magnetic field from that electromagnet passes. The falloff factor (FF) is an index that reflects what percent of an energy source is present after having traveled 1 cm from its previous position. The % of power at each time period ($T_n$) reflects the energy applied to the coil (duration and power)? As shown, at the Mutual Deep Target (which is the target at the intersection of the plurality of the stimulation provided by the electromagnets), the percent power is 115%, which is suprathreshold. In the case of 70 mm double coils that may be used for TMS, this factor is approximately 0.50 (fifty percent). Percent power at Mutual Deep Target is the percent of target activation threshold or percent motor threshold. As previously designated, Tn (e.g., T1, T2 . . . Tn) is an arbitrary time: these times may be equally spaced, but are not necessarily so. Percent power shown at Mutual Deep Target may be calculated at each Tn as:

Percent Power at $MDT = (FF^{DTDT} \times \%$ Power at $T_n)_{Coil\ A} + (FF^{DTDT} \times \%$ Power at $T_n)_{Coil\ B} + (FF^{DTDT} \times \%$ Power at $T_n)_{Coil\ C} + (FF^{DTDT} \times \%$ Power at $T_n)_{Coil\ D}$ Because the cingulate is a bilateral structure that happens to be close to the midline, such distances may be used for both the right and left cingulate structures if target is assumed to be (for the sake of easy calculate) a point between to two cingulate bundles. In the specific scenario illustrated with the particular values shown in the table, it is illustrated that two coils in which the underlying sulci are 2.5 cm from the target plus two coils in which the underlying sulci are 0.5 cm from the target, only 65% power is required from each coil to produce 115% of motor threshold at the target. Of course many other power/distance requirements may be determined with the method shown in this figure. A variant of the method illustrated by this table may be used to separately calculate the effect upon only one target at a time, based upon the distance of that target from each of the energy sources.

As mentioned above, any of the Transcranial Magnetic Stimulation (TMS) systems described herein are typically configured so that each electromagnet is individually controlled or instructed. Thus, these systems may include a controller that specifically coordinates each individual electromagnet, and the individual electromagnets are configured to be capable of acting independently of the others, so that each electromagnet may execute a separate stimulation protocol from the other electromagnets. The controller, which may be a separate component or an integrated component in the system, and may include both hardware and software (or firmware), typically executes a stimulation strategy that includes instructions for the control of each electromagnet. These instructions may include controlling the position, frequency or rate of firing, strength of firing, duration of firing, shape of applied voltage/current (e.g., waveform shape), position (e.g., angle and/or distance from patient, orientation around the patient, and in some variations, movement of the electromagnet), and direction of electromagnetic field. The instructions for controlling stimulation executed by the controller may also be referred to as a treatment plan or treatment strategy. In addition to controlling the activity of each electromagnet, the treatment strategy may also include a stimulation pattern, indicating the pattern of firing of individual electromagnets. As used herein "individual" electromagnets may include sets (e.g. pairs, etc.) of electromagnets.

Figure 9:
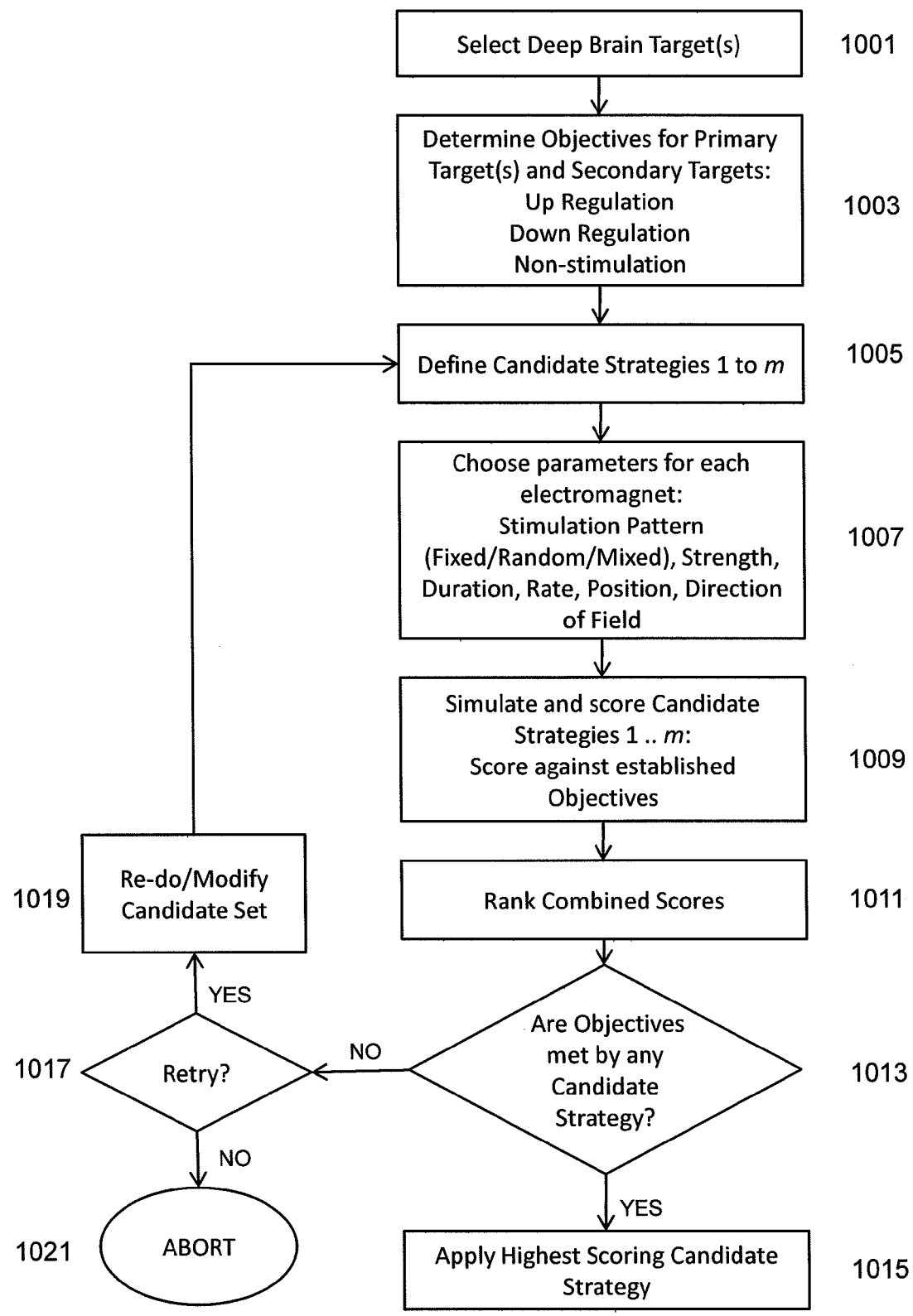
FIG. 9 is an flowchart showing one variation of a Transcranial Magnetic Stimulation method, as described herein.

In some variations the controller also includes logic (hardware and/or software) for generating the treatment strategy. Alternatively, a separate module or component for calculating the treatment strategy may be used. For example, scheduling logic may be used to generate one or more treatment strategies. FIG. 9 is a flowchart illustrating one method of generating a treatment strategy. In general, this treatment strategy is formulated by first determining (or inputting, e.g., by user input) the treatment objectives for each target region, as well as any other regions that may be affected by activation of the electromagnets, such as the brain regions between the electromagnet and the target.

Referring to FIG. 9, the first step in controlling a TMS system such as the systems described herein includes determining the deep brain tissue target(s) to be stimulated 1001. Any appropriate target may be chosen. The deep brain region target (e.g. sub-cortical target) may be chosen based on the treatment effect desired (e.g., treatment of depression, etc.). The target deep region of the subject's brain chosen may be provided to the controller (or other module) of the system by numeric (e.g., providing coordinates), by graphical (e.g., indicating on a subject's brain scan), or any other appropriate means. For example, the system may include brain scanning or mapping, or may receive input from brain scanning or mapping. For example, the system may receive the position or coordinates of the target(s) relative to the positions of the electromagnets. Once the primary target(s) (e.g., deep brain targets) have been determined, the system may determine what secondary targets may be affected by the stimulation of the target regions. A secondary target may also be called an incidental target or a collateral target, because, although it is not an intended target, it may be stimulated during the attempt to stimulate the intended target. For example, the cortical region between the deep brain region and the electromagnet, along the pathway of the pulse emitted by the electromagnet, may be considered a secondary or collateral target. In some cases, a collateral target may also be a primary target.

The position of the electromagnets (coils) around the subject may also be adjusted. For example, once the target deep brain region(s) have been selected, the coils around the subject heads may be moved to better reach them. In some variations, the magnets may be continuously moved (e.g., rotated, tilted, or otherwise repositioned) to reach the target region(s). The movement may be coordinated or controlled by the controller, and may be made either at the start of a treatment, or it may occur continuously or periodically during the treatment. Thus the treatment strategy may include control of magnet position and/or movement.

Once the primary target regions and collateral or secondary target regions have been identified, the system may then determine objectives for the primary and secondary targets 1003. The objective may be input from the user (e.g., doctor, technician, etc.) and/or may be selected form a database of objectives. In some variations, the objective for a particular region (e.g., target region) may be expressed as a level of stimulation desired, such as stimulation at a set frequency or range of frequencies (e.g., 5 Hz, 50 Hz, 100 Hz, 200 Hz, 500 Hz, etc.) or a predetermined pattern (e.g., bursts of pulses separated by a delay period). In some variations, the objectives may be broadly characterized as "up regulation", "down regulation" or "non-stimulation." For example, an objective of non-stimulation may be interpreted as limiting the target region (e.g., a collateral target region) so that threshold stimulation from the electromagnet (e.g., stimulation less than 100% MT for that region) is not achieved. Thus, although pulses may pass through the target region, they should not achieve 100% MT in that region. Similarly, an objective of "up-regulation" in a particular region may mean stimulation at a frequency of about 5 Hz or greater within the target region. Similarly, an objective of "down-regulation" of a target region may refer to stimulation at a rate of 1 Hz or less. An inventory or database of stimulation objectives for multiple different brain regions may be used (and may be included as part of the system) to provide an adjustable default or pre-set to the system. For example, the adjustable default for collateral targets may be non-stimulation.

Once targets and target objectives have been selected, the system may then apply a method to determine a stimulation strategy. One variation of such a method is shown in FIG. 9, steps 1005-1019. For example, the system may generate a plurality of candidate strategies 1005 (e.g., m candidate strategies) by applying the target strategies, then score these strategies after simulating their application, and apply the highest-scoring treatment strategy.

Figure 11:
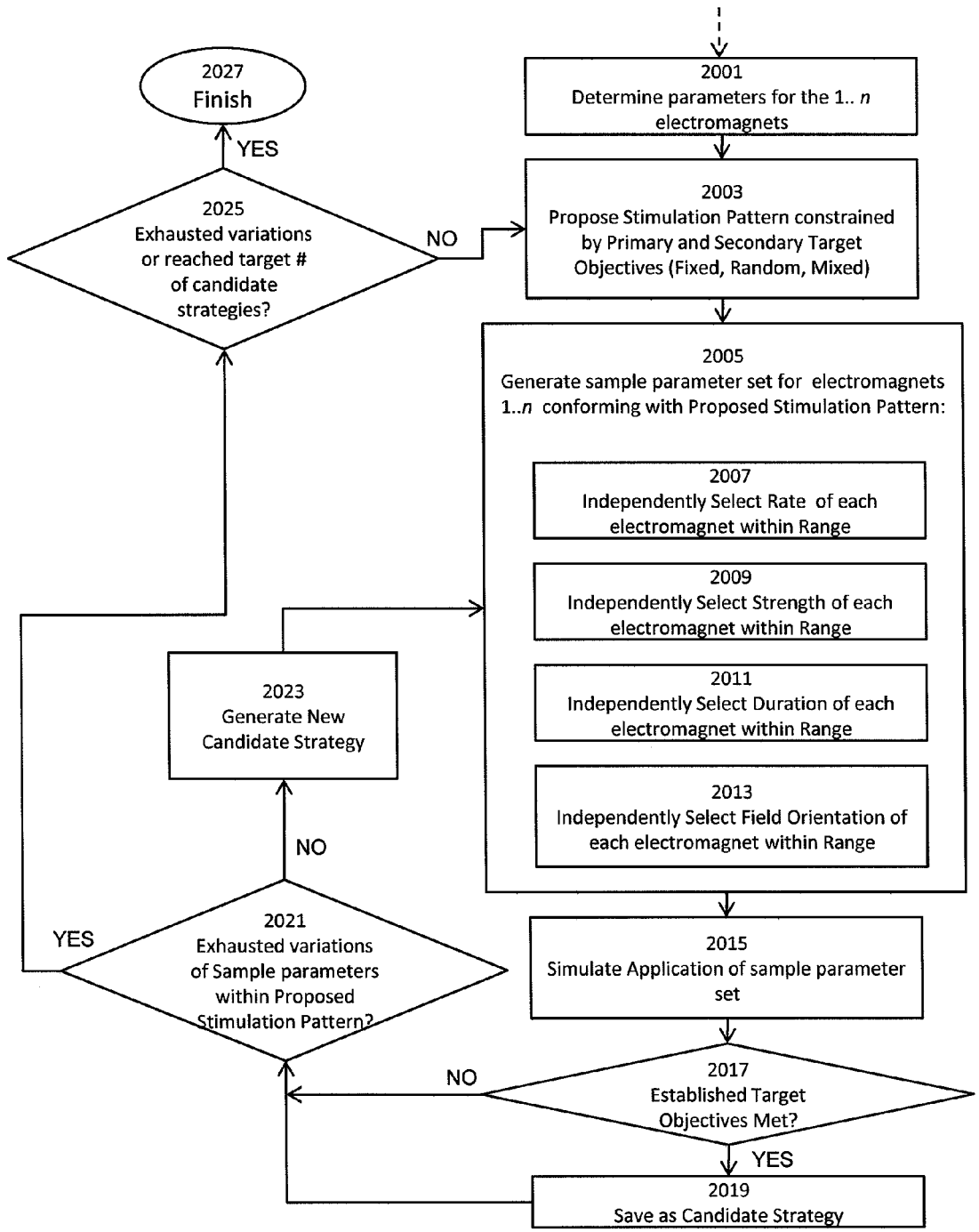
FIG. 11 is one variation of a portion of a method of determining stimulation parameters for Transcranial Magnetic Stimulation.

FIG. 11 provides one illustration of a method for choosing parameters for candidate strategies, as indicated in steps 1005 and 1007. In general, the step of choosing parameters for each magnet during a treatment strategy may include generating a stimulation pattern wherein the timing of firing of each magnet in the system is coordinated. This stimulation pattern may be fixed, random or mixed, as described above. Further, the firing characteristics of each electromagnet during the stimulation pattern may be selected, including strength, duration, shape of the applied waveform, position of the electromagnet, direction of the field, etc. These parameters (the stimulation pattern and the firing characteristics) may be constrained by the target and target objectives. For example, FIG. 11, steps 2001-2027, describes one variation of a method of determining generating a target number of candidate stimulation strategies. For example, permutations of strength, duration, rate, field orientation, etc. may be determined 2005 for different permutations of stimulation patterns 2003, and simulated 2015 to determine if they achieve the target objectives 2017 for both primary and collateral targets. This process can be iteratively repeated until an array of candidate strategies (or a best candidate strategy, if they are being scored and compared during this process) is identified. In some variations, pre-set or historical treatment strategies may be applied or used as a starting point for determining a candidate treatment strategy. For example, a database of treatment strategies for particular targets may be used. Thus, in some variations, the system may include such a database, and may add to or modify this database.

Simulation of a candidate treatment plan (e.g., during determination of a treatment plan, as shown in FIG. 11, or during scoring of a treatment plan, as shown in FIG. 9, may be based on the application of the summation (both temporal and spatial) of the applied pulse(s) within each target region. For example, as indicated by FIG. 8, described above, a matrix of simulated stimulation values may be generated to determine what the rate and level of stimulation is for each target region, which can then be compared against the objectives for that target region. Thus, the simulation may apply the attenuation factor, based on the location of the target region relative to the electromagnets. In some variations, particular characteristics of the tissue may also be applied (e.g., region attenuation factors, regional thresholds for stimulation, the effect of field orientations in certain regions, etc.).

Figure 10:
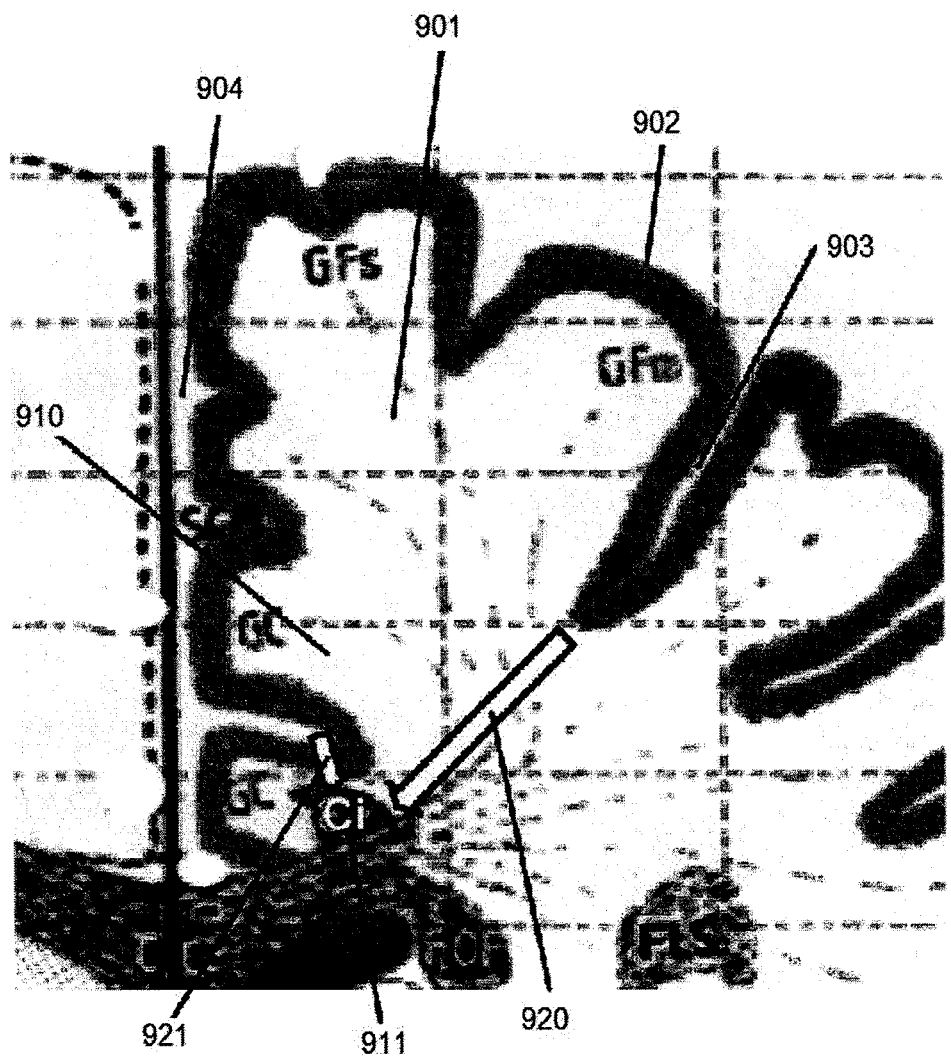
FIG. 10 illustrates distances measured from the bottom of cortical sulci to a deep target, in this example, the cingulate bundle.

FIG. 10 is an adaptation of a figure from the Talairach Atlas in which distances are measured from the bottom of a cortical sulci to a deep target, in this case the cingulate bundle. Brain 901 includes gyrus 902 (a representative example), sulci 903

(a representative example), and longitudinal fissure 904. Sulci 903 and longitudinal fissure 904 are typically filled with clear cerebrospinal fluid (not illustrated). Cerebrospinal fluid is composed principally of water with sodium chloride salt, which makes these spaces highly electrically conductive. Inside brain 901 is also the cingulum: principally gray matter but also containing cingulate bundle 910, which is composed of axons, or white matter. The distances between the deep target (e.g., cingulate bundle 911) and the bottom of two nearby highly conductive sulci are relatively short: distance 911 and distance 920. Distance 911 and distance 920, when represented in centimeters, may be used within the context of the table in FIG. 8 as DTDT (distance to deep target) numbers. Because the cingulate is a bilateral structure that happens to be close to the midline, such distances may be used for both the right and left cingulate structures if target is assumed to be a point between to two cingulate bundles.

In accordance with the method described, even though there may be radical difference in way the different sources (e.g. coils) behave, the net results at various locations may still be predicted and controlled. Fast and slow stimulation rates may be simultaneously applied to neural tissue on the periphery, while either fast or slow stimulation is being applied to the shared deep target. While the examples of electromagnets shown in the figures are V-shaped double TMS coils, the present method is intended to be generic to any neurostimulation energy source, including, but not limited to standard (flat) double TMS coils or circular TMS coils. The method is also intended to generically apply to neurostimulation energy sources including but not limited to direct or alternating current electrodes, optical neurostimulation light sources, and ultrasound emitters, any of which may be either implanted, externally placed, or within natural orifices.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. Such modifications and changes do not depart from the true spirit and scope of the present invention, which is set forth in the following claims.

REFERENCES

Huang, Y-Z, Edwards, M. J. Rounia, Elizabeth, Bhatia, K. P., and J. C. Rothwell, "Theta Burst Stimulation of the Human Motor Cortex," Neuron, 45:201-206, 2005.
U.S. patent application Ser. No. 10/821,807 "Robotic apparatus for targeting and producing deep, focused transcranial magnetic stimulation," Schneider M B and Mishelevich D J.
Mishelevich D J, Schneider M B, U.S. patent application Ser. No. 11/429,504 "Trajectory-Based Deep-Brain Stereotactic Transcranial Magnetic Stimulation," WO 2007130308 20071115
Ruohonen J, Ilmoniemi R J. Focusing and targeting of magnetic brain stimulation using multiple coils. Med. Biol eng. Comput., 1998, 36, 297-301.
Ruohonen J, Ravazzani P, Grandori F, Ilmoniemi R. Theory of Multichannel Magnetic Stimulation: Toward Functional Neuromuscular Rehabilitation. IEEE Transactions on biomedical Engineering, Vol 46, No. 6, June 1999. 646-651
Han B, Chun I K, Lee S C, Lee S Y. Multichannel Magnetic Stimulation System Design Considering Mutual Coupling Among the Stimulating Coils. IEEE Transactions on Biomedical Engineering. Vol 51. No. 5, May 2004. 812-817
Mishelevich D J, Schneider M B. Pulsing Multiple Independently Triggered Electromagnets from One or More Energy Sources, USPTO 60970958, Sep. 9, 2007
Schneider M B, Mishelevich D J Target-Specific Coil Configurations for Transcranial Magnetic Stimulation. USPTO 60990300. Nov. 27, 2007.
Isenberg K, Downs D, Pierce K, Svarakic D, Garcia K, Jarvis M, North C, Kormos TC. Low frequency rTMS stimulation of the right frontal cortex is as effective as high frequency rTMS stimulation of the left frontal cortex for antidepressant-free, treatment-resistant depressed patients. Ann Clin Psychiatry. 2005 July-September; 17(3):153-9.
Talairach J, Tournoux P (1988). Co-planar stereotaxic atlas of the human brain. Thieme, N.Y.
Voxel-Man 3D Navigator V. 2.0 Karl Heinz Hohne and Springer Verlag Electronic Media. Heidelberg, Germany 2001.

What is claimed is:

1. A Transcranial Magnetic Stimulation (TMS) method for stimulating a primary brain target of neuronal tissue deep within a subject's brain by firing a plurality of electromagnets located at different locations around the subject's head at different secondary targets, the method comprising:
    firing a first electromagnet with a first duration, rate and power to emit an electromagnetic pulse and stimulate a first secondary brain target connected to a target deep region of the subject's brain along a first pathway through the subject's brain;
    firing a second electromagnet following a waiting period after the firing of the first electromagnet has finished, wherein the second electromagnet is fired with a second duration, rate and power to emit an electromagnetic pulse and stimulate a second secondary brain target connected to the target deep region of the subject's brain along a second pathway through the subject's brain;
    wherein the first duration, rate and power are different from the second duration, rate and power; and
    triggering stimulation in the target deep region of the subject's brain located in an intersection of the first and second pathways through the first and second pathways.

2. The method of claim 1, further comprising:
    determining the first duration, rate and power for firing the first electromagnet; and
    determining the second duration rate and power for firing the second electromagnet, wherein the first and second duration rate and power are determined based on an attenuation factor and a distance to the target deep region in the subject's brain from the first and second electromagnets.

3. The method of claim 1, wherein the step of firing the first electromagnet comprises firing the first electromagnet at the first duration, rate and power without triggering stimulation of neural tissue located more superficially to the target deep region.

4. The method of claim 1, further wherein the step of firing the second electromagnet comprises firing the second electromagnet at the second duration, rate and power without triggering stimulation of neural tissue located more superficially to the target deep region.

5. The method of claim 1, wherein of the first duration is determined independently of the second duration, the first rate is determined independently of the second rate, and the first power is determined independently from the second power.

6. The method of claim 1, wherein the step of firing the first electromagnet comprises firing the first electromagnet from a stationary electromagnet that is not configured to move during a TMS treatment.

7. The method of claim 1, wherein the step of firing the first electromagnet comprises firing the first electromagnet from a movable electromagnet that is configured to move during a TMS treatment.

8. The method of claim 1, further comprising firing a third electromagnet at a third duration, rate and power to emit an electromagnetic pulse and stimulate a third secondary brain target connected to the deep target region along a third pathway through the subject's brain, wherein the third pathway intersects with the first and second pathways at the target deep region of the subject's brain.

9. The method of claim 8, wherein the step of triggering stimulation in the target deep region of the subject's brain further comprises temporally and spatially summing an effect of the electromagnetic pulses emitted by the first, second, and third electromagnets on the target deep region of the subject's brain.

10. The method of claim 1, further comprising triggering stimulation in the target deep region of the subject's brain at a predetermined rate by firing bursts of electromagnetic pulses from the first and second electromagnets that stimulate the first and second secondary brain targets, wherein the first and second secondary brain targets trigger stimulation within the target deep region, wherein the bursts of pulses are separated by a waiting period during which electromagnetic pulses from the first and second electromagnets do not sum to trigger stimulation in the target deep region.

11. The method of claim 1, wherein the steps of firing the first electromagnet and firing the second electromagnet comprise powering the first electromagnet and the second electromagnet from a first power source.

12. The method of claim 1, wherein the steps of firing the first electromagnet and firing the second electromagnet comprise powering the first electromagnet and the second electromagnet from different power sources.

13. A Transcranial Magnetic Stimulation (TMS) method for stimulating a primary brain target of neuronal tissue deep within a subject's brain by firing a plurality of electromagnets located at different locations around the subject's head at different secondary targets, the method comprising:

firing a first electromagnet with a first stimulation pattern so that a plurality of electromagnetic pulses are emitted and stimulate a first secondary brain target connected to a target deep region of the subject's brain along a first pathway;

asynchronously firing a second electromagnet following a waiting period after the firing of the first electromagnet has finished, wherein the second electromagnet is fired with a second stimulation pattern so that a plurality of electromagnetic pulses are emitted and stimulate a second secondary brain target connected to the target deep region of the subject's brain along a second pathway;

triggering a pattern of stimulation at the target deep region of the subject's brain located in an intersection of the first and second pathways through the first and second pathways.

14. A Transcranial Magnetic Stimulation (TMS) method for stimulating a primary brain target of neuronal tissue deep within a subject's brain by firing a plurality of electromagnets located at different locations around the subject's head at different secondary targets, the method comprising:

firing a first electromagnet with a first duration, rate and power to emit an electromagnetic pulse and stimulate a first secondary brain target connected to a deep target region along a first pathway through the subject's brain;

firing a second electromagnet with a second duration, rate and power to emit an electromagnetic pulse and stimulate a second secondary brain target connected to the deep brain target region along a second pathway through the subject's brain;

wherein the first duration, rate and power are different from the second duration, rate and power; and triggering stimulation in the target deep region of the subject's brain located in an intersection of the first and second pathways through the first and second pathways.

\* \* \* \* \*